United States Patent
Karino et al.

(10) Patent No.: US 7,201,748 B2
(45) Date of Patent: Apr. 10, 2007

(54) ENERGY IRRADIATION APPARATUS

(75) Inventors: Wataru Karino, Ashigarakami-gun (JP); Akira Sakaguchi, Ashigarakami-gun (JP); Hiroshi Kizukuri, Yachiyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 354 days.

(21) Appl. No.: 10/809,547

(22) Filed: Mar. 26, 2004

(65) Prior Publication Data
US 2005/0010199 A1 Jan. 13, 2005

(30) Foreign Application Priority Data

| | | | |
|---|---|---|---|
| Mar. 27, 2003 | (JP) | ............................ | 2003-089008 |
| Mar. 27, 2003 | (JP) | ............................ | 2003-089009 |

(51) Int. Cl.
*A61B 18/20* (2006.01)
(52) U.S. Cl. ............................. 606/14; 606/15; 606/18
(58) Field of Classification Search ................... 606/7, 606/10–19; 607/88, 89, 92
See application file for complete search history.

(56) References Cited

U.S. PATENT DOCUMENTS

| | | | | |
|---|---|---|---|---|
| 5,242,438 A | * | 9/1993 | Saadatmanesh et al. | ....... 606/15 |
| 5,380,317 A | * | 1/1995 | Everett et al. | ................. 606/15 |
| 5,496,307 A | * | 3/1996 | Daikuzono | ................... 606/15 |
| 5,833,683 A | * | 11/1998 | Fuller et al. | ................... 606/17 |
| 6,379,347 B1 | | 4/2002 | Maki et al. | |
| 6,562,029 B2 | | 5/2003 | Maki et al. | |
| 6,579,286 B1 | | 6/2003 | Maki et al. | |
| 6,599,287 B2 | * | 7/2003 | Iwahashi et al. | ............... 606/14 |
| 6,889,116 B2 | * | 5/2005 | Jinno | ......................... 700/245 |
| 2002/0022829 A1 | | 2/2002 | Nagase et al. | |

FOREIGN PATENT DOCUMENTS

| | | | |
|---|---|---|---|
| EP | 0 673 627 A1 | | 9/1995 |
| EP | 1 072 231 A1 | | 1/2001 |
| EP | 1 075 852 A2 | | 2/2001 |
| EP | 1 075 853 A2 | | 2/2001 |
| EP | 1 462 147 A1 | * | 9/2004 |
| JP | 2004-290520 A | * | 10/2004 |

* cited by examiner

*Primary Examiner*—A. Farah
(74) *Attorney, Agent, or Firm*—Buchanan Ingersoll & Rooney PC

(57) ABSTRACT

This invention is directed to an energy irradiation apparatus including an insertion portion (3) which includes a hollow cylindrical member (14) having a sealed distal end portion and is inserted into a living body, and an energy irradiation portion (20) which applies energy to living tissue through an irradiation window portion (17) which is provided on a side wall of the hollow cylindrical member (14) to extend in the longitudinal direction. This apparatus includes a driving unit which reciprocates with substantially a constant velocity the laser irradiation portion (20) in the direction indicated by an arrow D along the longitudinal direction of the irradiation window portion (17). With this structure, the energy irradiation apparatus can uniformly irradiate a lesion with energy.

13 Claims, 19 Drawing Sheets

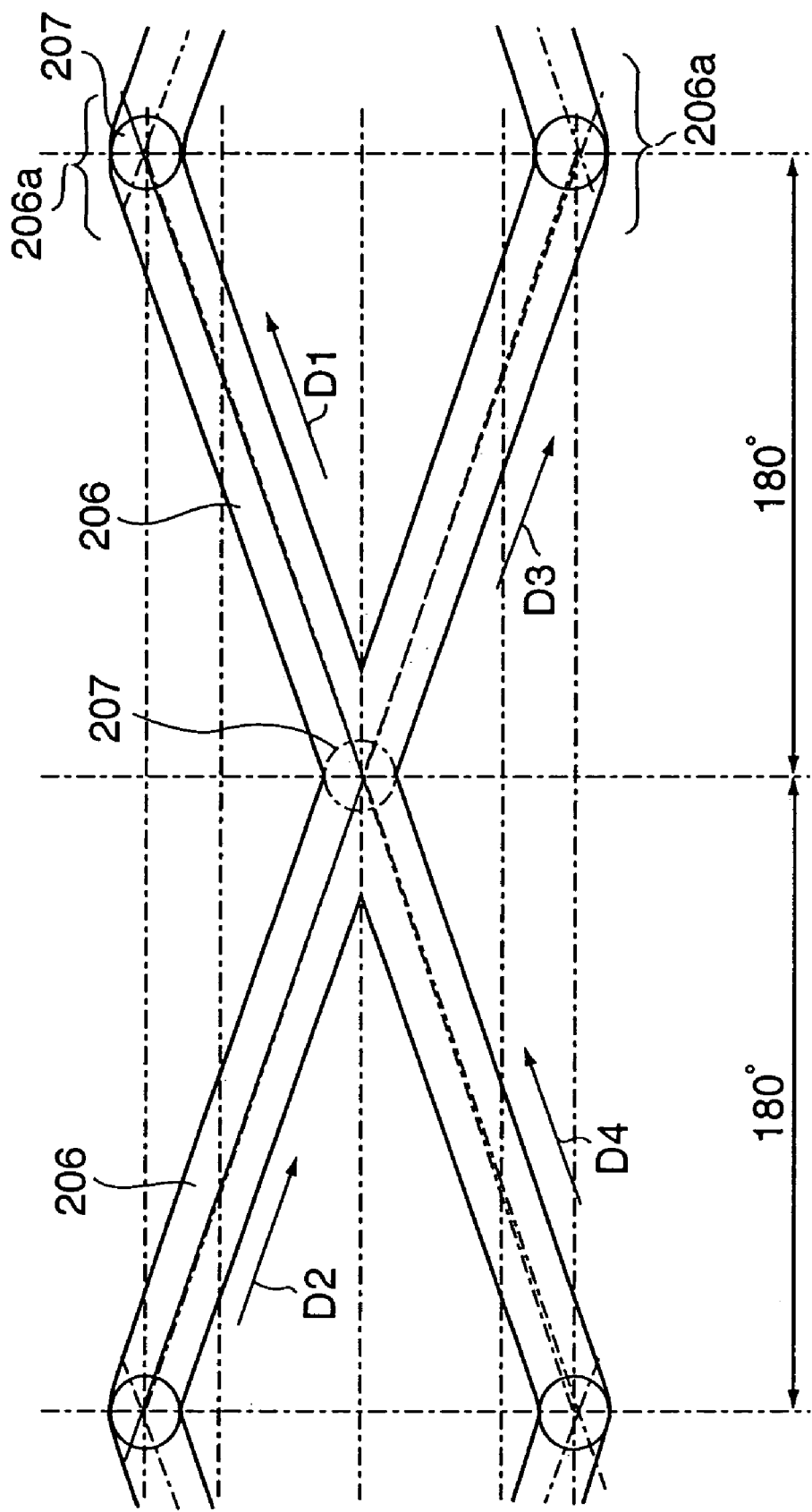

ENERGY IRRADIATION APPARATUS

CLAIM OF PRIORITY

The present application claims priority under 35 U.S.C. § 119 from Japanese Patent Application No. 2003-89008 and No. 2003-89009, both entitled "An Energy Irradiation Apparatus" and both filed on Mar. 27, 2003, the entire contents of which are hereby incorporated by reference herein.

FIELD OF THE INVENTION

The present invention relates to an energy irradiation apparatus which inserts an insertion portion into a lumen such as a blood vessel, an alimentary canal, for example, an esophagus or rectum, an urethra, or an abdominal cavity, and irradiates living tissue with energy to perform heating treatment.

BACKGROUND OF THE INVENTION

An energy irradiation apparatus is used to eliminate or to cure a lesion in a living body by inserting an elongated insertion portion into the living body through a lumen or a small incision made in the living body, selectively irradiating the lesion with energy, and causing heating, denaturation, necrosis, coagulation, cauterization, or vaporization of the tissue of the lesion. Such an energy irradiation apparatus is generally designed to directly irradiate a lesion located on or near the surface layer of living tissue with energy.

In addition, a technique of irradiating a deep region in living tissue with energy is also known, which is used to cure a lesion located deep in living tissue, that is, a deep lesion, as in thermal treatment for benign prostatic hyperplasia, by directly inserting an energy irradiation portion into a deep lesion inside the prostate by puncture.

The prostate is located in the basal region of the bladder of a male, surrounding the posterior portion of the urethra. When energy irradiation treatment is to be performed for benign prostatic hyperplasia, a transurethal technique is often used. However, irradiation of energy through the urethra for a long period of time or inserting a needle-like energy irradiation portion through the urethra damages the surface of the urethra. This may cause an infectious disease through the wound.

In consideration of such a problem, an apparatus which concentrates energy having deep transmission capability against living tissue onto a deep portion while continuously moving the energy exit end portion has been proposed as an apparatus which cures only the affected part of the prostate without damaging the surface of the urethra. Such energy concentrating apparatuses are disclosed in Japanese Patent Laid-Open Nos. 11-333005, 2000-319, and 2001-46396.

According to an apparatus designed to concentrate energy having deep transmission capability against living tissue as described in each of the patent references described above, the energy irradiation end portion is periodically reciprocated to disperse energy on the surface layer of the urethra so as to preserve the tissue. On the other hand, energy is concentrated onto a deep portion as a lesion of living tissue to provide effective heating treatment.

Such an apparatus uses a reciprocating mechanism having a link. One end of the link is supported on a disk which is rotated/driven to produce periodic reciprocating motion, while the other end of the link is supported on a moving member which is reciprocated. With this structure, reciprocating motion becomes angular velocity motion. As a consequence, unbalanced velocities occur near the middle and two ends of reciprocation.

If energy irradiation is performed by using the reciprocating mechanism which produces low velocities near the two ends of reciprocation and the highest velocity near the middle, energy is radiated for a long period of time near the two ends of reciprocation. This may locally heat the surface layer of the urethra and then results in failure to preserve the surface layer tissue or results in failure to obtain a sufficient treatment effect.

SUMMARY OF THE INVENTION

The present invention has been made in consideration of the above problems, and has as its object to provide an energy irradiation apparatus which can uniformly irradiate a lesion with energy.

It is another object of the present invention to provide an energy irradiation apparatus which can preserve the normal living tissue of the surface layer by uniformly irradiating only a deep portion of a lesion of living tissue with energy.

In order to solve the above problems and achieve the above objects, according to the present invention, there is provided an energy irradiation apparatus comprising an insertion portion which includes a hollow cylindrical member having a sealed distal end portion and is inserted into a living body, and an energy irradiation mechanism which is placed inside the hollow cylindrical member and radiates energy to living tissue through an irradiation window portion which is provided on a side wall of the hollow cylindrical member to extend in a longitudinal direction, wherein the energy irradiation mechanism comprises an energy irradiation end portion which is placed facing the irradiation window portion and reciprocating along the longitudinal direction of the irradiation window portion, and a driving unit which drives the energy irradiation end portion to make reciprocating motion with substantially a constant velocity.

In addition, according to the present invention, there is provided an energy irradiation apparatus comprising an insertion portion which includes a hollow cylindrical member having a sealed distal end portion and is inserted into a living body, and an energy irradiation mechanism which is placed inside the hollow cylindrical member and radiates energy to living tissue through an irradiation window portion which is provided on a side wall of the hollow cylindrical member to extend in a longitudinal direction, wherein the energy irradiation mechanism comprises an energy irradiation end portion which is placed facing the irradiation window portion and reciprocating along the longitudinal direction of the irradiation window portion, a transmitting member which transmits a reciprocation in a major axis direction of the insertion portion to cause the energy irradiation end portion to make reciprocating motion, a cylinder which is held to be rotatable about an axis parallel to an axis in the longitudinal direction and has a shaped portion which is formed on an outer surface and reciprocates the transmitting member, and a driving unit including a motor which rotates the cylinder.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 13 is a developed view showing an endless groove portion 206 formed in the outer surface of a cylindrical member of a driving unit 55 according to the seventh embodiment with the groove portion being developed 360°;

DETAILED DESCRIPTION OF THE PREFERRED EMBODIMENTS

Each embodiment of the present invention will be described below with reference to the accompanying drawings by exemplifying a laser irradiation apparatus and ultrasonic irradiation apparatus, each as one of energy irradiation apparatuses.

A. Arrangement Common to Each Embodiment

Figure 1:
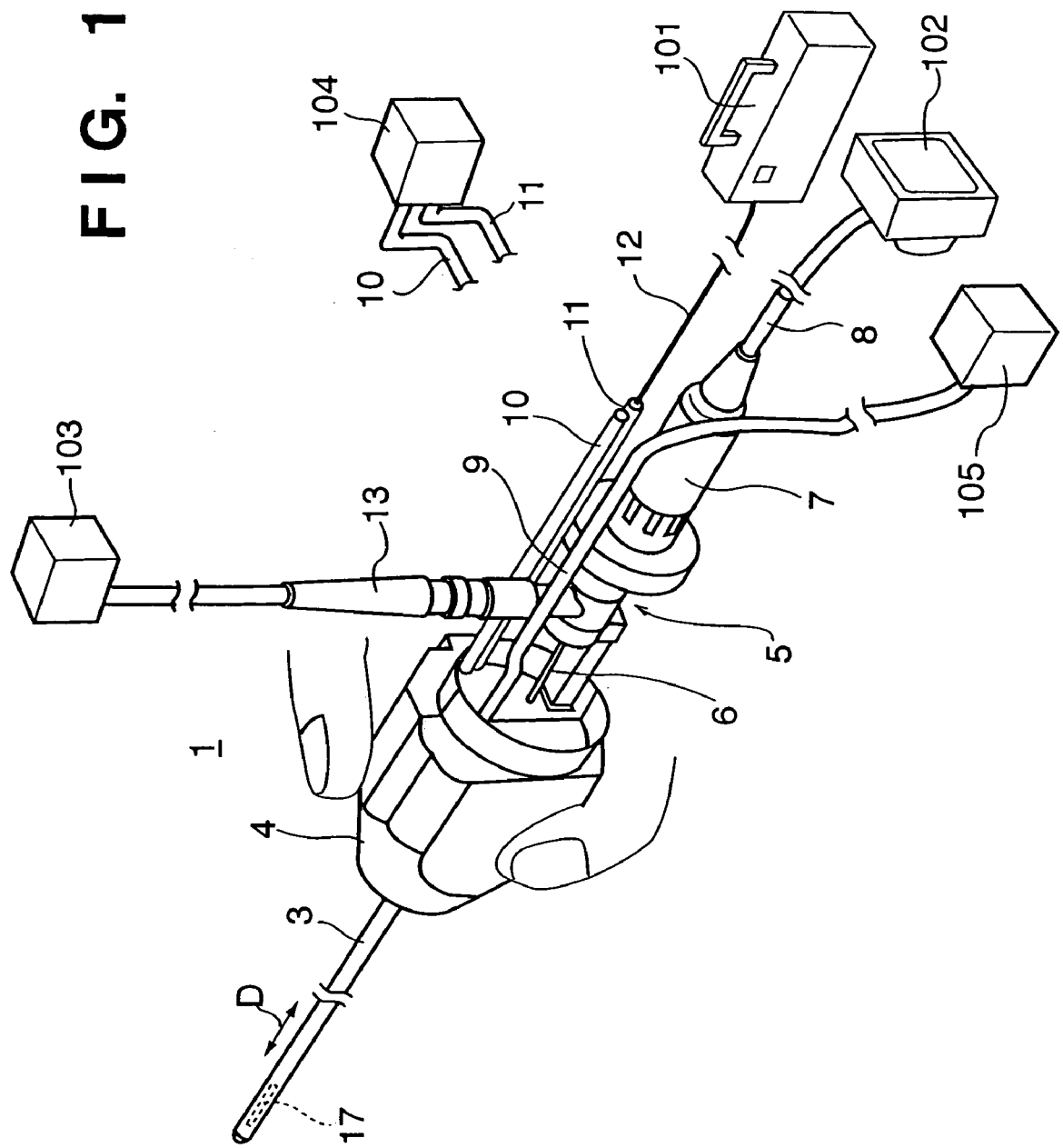
FIG. 1 is a perspective view showing the overall arrangement of a laser irradiation apparatus 1.

FIG. 1 is a perspective view showing the overall arrangement of a laser irradiation apparatus 1. FIG. 1 is almost common to the respective embodiments to be described below. Referring to FIG. 1, the laser irradiation apparatus 1 is of a side-emitting type which is used for medical treatment of a deep portion of the affected part of the living body. This apparatus is used for medical treatment of, for example, benign prostatic hyperplasia by irradiating the affected part of the living body with a laser beam as energy. In addition to this type, there is available an ultrasonic type to be described later as a type which makes medical treatment of a surface layer portion of living tissue.

The laser irradiation apparatus 1 irradiates a deep portion of living tissue with a laser beam through an insertion portion 3 and irradiation window portion 17. The insertion portion 3 is formed by sealing the distal end of a long hollow cylindrical member which can be inserted into the living body. As indicated by the broken lines, the irradiation window portion 17 extends on a side wall of the insertion portion 3 in the longitudinal direction so as to transmit a laser beam. The outer diameter of the insertion portion 3 is about 2 to 20 mm, and more preferably about 3 to 8 mm, which allows insertion into a body cavity. The insertion portion 3 is inserted through the urethra of a male to make medical treatment of benign prostatic hyperplasia. The thinner the insertion portion 3 becomes, therefore, the more the pain to the patient is reduced.

As shown in FIG. 1, the insertion portion 3 is fixed to a cover portion 4 which is grasped by a doctor to, for example, insert the insertion portion 3. In addition, the proximal end of an optical fiber 12 pulled out from the insertion portion 3 is connected to a laser source device 101 through an optical connector (not shown). An observation device 5 for the observation of the surface of living tissue is attached to the laser irradiation apparatus 1. The observation device 5 has an endoscope 6 which can be detachably mounted in the laser irradiation apparatus 1. The endoscope 6 is inserted from the proximal end side of the cover portion 4, and is placed in the insertion portion 3 so as to be movable in the longitudinal direction.

The endoscope 6 includes, for example, an optical fiber bundle, a protective tube, and an imaging lens mounted on the distal end. A CCD camera head 7 is attached to the proximal end side of the endoscope 6. This makes it possible to send an image to a monitor device 102 through a camera signal lead 8. In addition, the optical fiber of the endoscope 6 also has a function of radiating illumination light sent through a lightguide 13 connected to a light source device 103.

The insertion portion 3 incorporates two channel chambers. A water supply/drain device 104 is connected to a water supply tube 11 and drain tube 10 connected to these channel chambers. The water supply/drain device 104 is used to supply and drain sterilized purified water or sterilized physiological saline as a cleaning liquid as well as coolant. The optical fiber 12 is also incorporated in the insertion portion 3 so as to be reciprocated/driven in the longitudinal direction (the direction indicated by an arrow D). A power supply device 105 for energizing a driving motor for reciprocating/driving the optical fiber 12 is connected to the insertion portion 3 through a lead 9.

Figure 2:
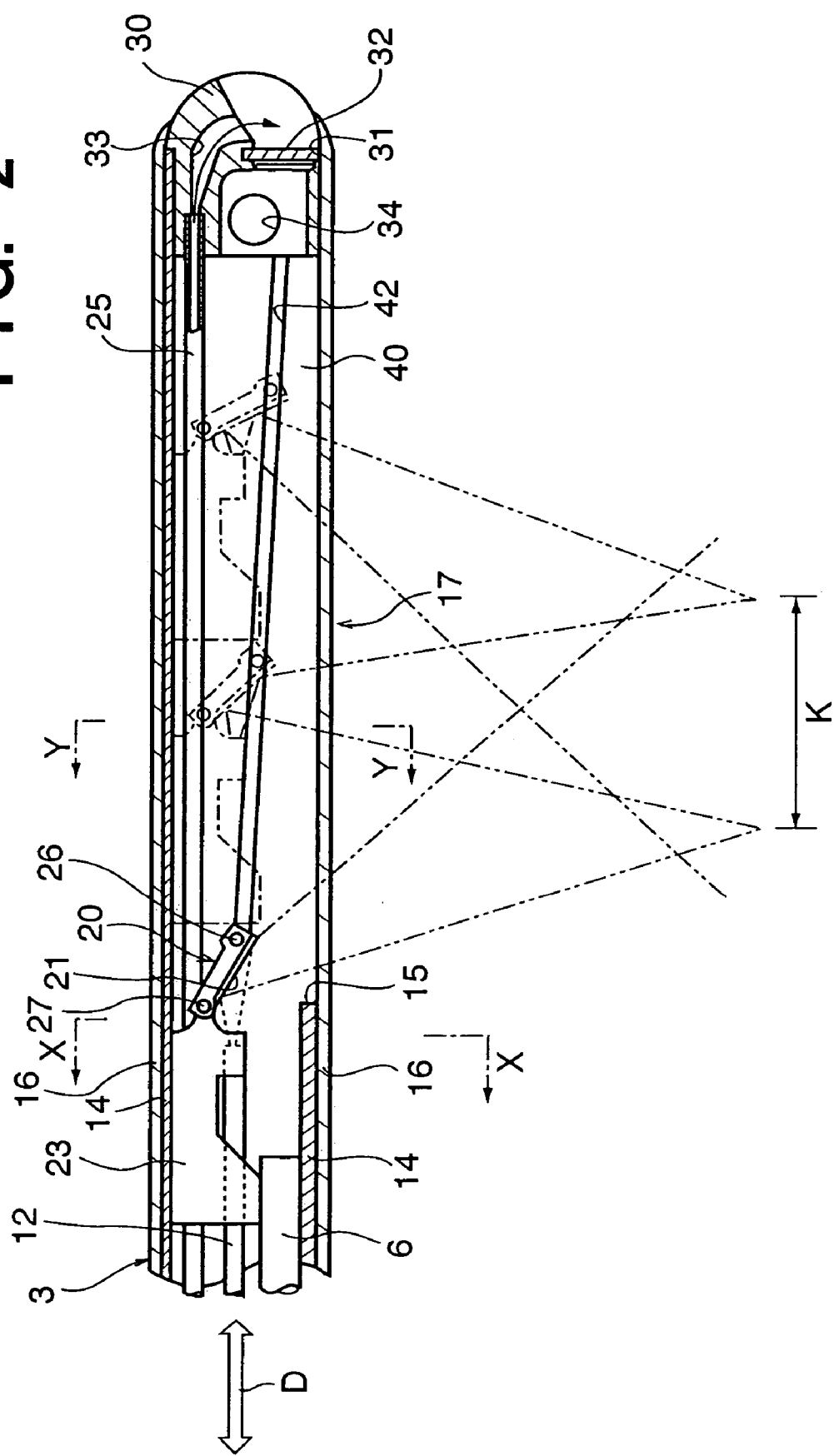
FIG. 2 is a central sectional view of an insertion portion 3.
Figure 3:
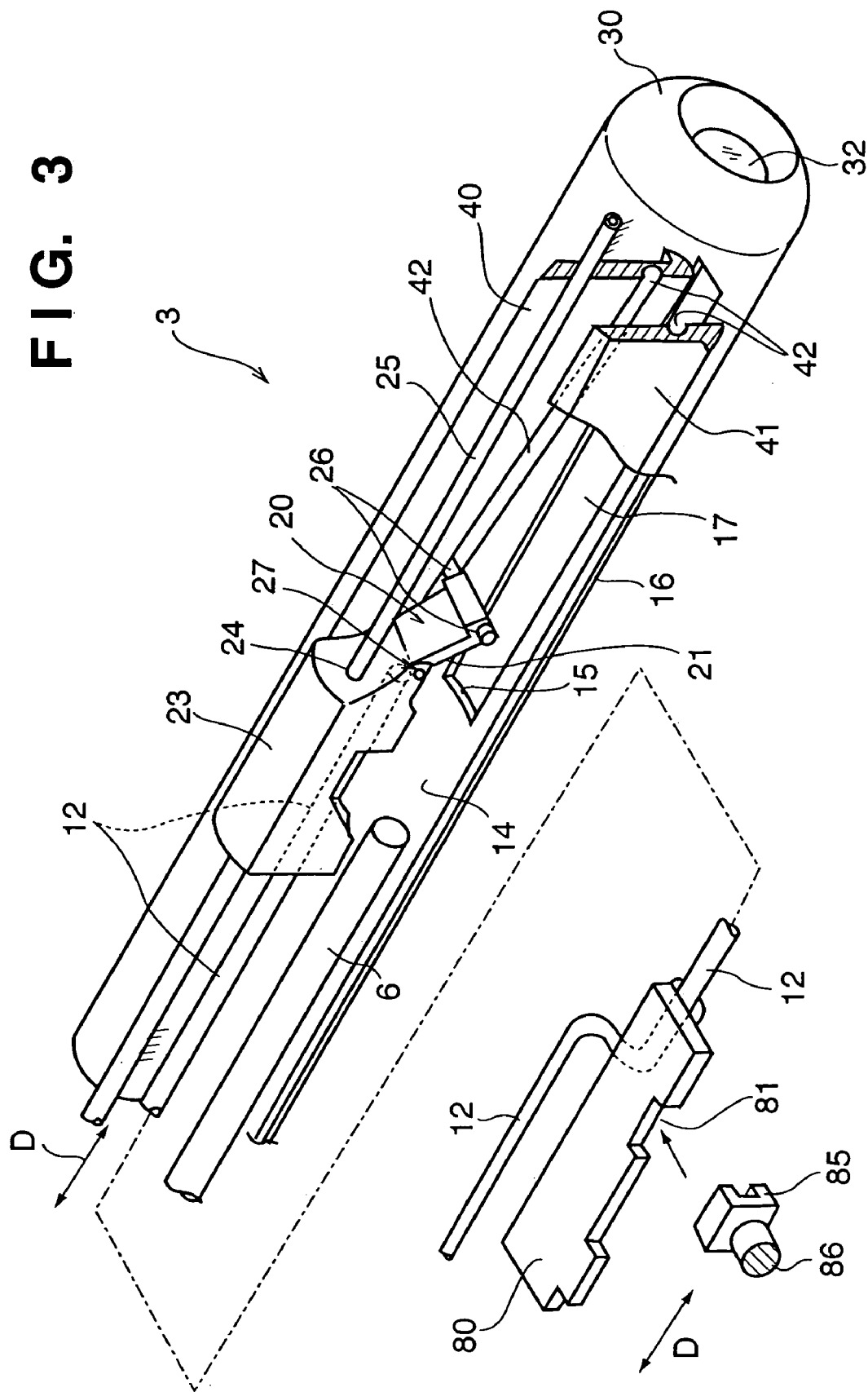
FIG. 3 is a perspective view showing the internal arrangement of the portion in FIG. 2.

FIG. 2 is a central sectional view of the insertion portion 3. FIG. 3 is a perspective view showing an internal arrangement. The same reference numerals as in FIGS. 2 and 3 denote the same parts described above, and a description thereof will be omitted. The insertion portion 3 has a long hollow cylindrical member 14 as a basal part, in which a laser irradiation mechanism 20 is provided. The laser irradiation mechanism 20 is designed to direct the laser beam output from the exit of the optical fiber 12, which transmits a laser beam, to the irradiation window portion 17 by causing a mirror 21 serving as a laser exit end portion and having a smooth laser reflecting surface to reflect the laser beam. The hollow cylindrical member 14 of the insertion portion 3 is made of a hard pipe material such as stainless steel. An opening 15 is formed in the surface of the distal end of the hollow cylindrical member 14. The entire outer surface of the hollow cylindrical member 14 including the opening 15 is covered with an outer tube 16 having good laser transmittance properties. The irradiation window portion 17 is arranged while the hollow cylindrical member 14 is covered with the outer tube 16.

A cap 30 is airtightly fixed to the distal end of the hollow cylindrical member 14. The cap 30 is also provided with a front window 31 for allowing the operator to observe ahead when the insertion portion 3 is inserted into a living body. A transparent plate 32 having good light transmission properties is fixed to the front window 31. A pair of wall members 40 and 41 which define an internal space are provided inside the distal end portion of the insertion portion 3.

The mirror 21 of the laser irradiation mechanism 20 is made of, for example, a resin, glass, or metal, or a composite material thereof. More specifically, this mirror is formed by, for example, polishing the surface of a base material made of a metal into a mirror surface, coating a base material made of a resin or metal with a thin metal film or the like by deposition to form a mirror surface, or bonding a reflecting member such as a glass mirror to a base material made of a resin, metal, or the like.

The optical fiber 12 which transmits a laser beam is placed in the insertion portion 3. In the insertion portion 3, the optical fiber 12 is covered with a protective pipe made of, for example, stainless steel, except for the distal end portion, to prevent breakage or a bend. The light exit of the optical fiber 12 is fixed to a reciprocating member 23 with which the mirror 21 is pivotally provided.

A through hole 24 (see FIG. 3) is formed in the reciprocating member 23 in the longitudinal direction. A monorail pipe 25 kept parallel to the axis of the insertion portion 3 extends through the through hole 24 to movably guide the reciprocating member 23 in the direction indicated by an arrow D in FIG. 2. Guiding the reciprocating member 23 along the monorail pipe 25 in this manner gives reciprocating force to the reciprocating member 23 with respect to the optical fiber 12, thereby making the reciprocating member 23 stably slide parallel to the axis of the insertion portion 3.

The mirror 21 is pivotally and axially supported on the reciprocating member 23 with a pair of pivoting portions 27, and has a pair of projections 26 extending from the two side portions of the distal end. The projections 26 are inserted in a pair of grooves 42 formed in the wall members 40 and 41 to be slidably supported. As shown in FIGS. 2 and 3, the grooves 42 tilt with respect to the axial direction of the insertion portion 3. For this reason, as the optical fiber 12 reciprocates, the mirror 21 reciprocates while changing its tilt angle owing to the effect of slidable contact with the grooves 42. As a result, laser beams are output from the irradiation window portion 17 along the laser loci indicated by the chain double-dashed lines in FIG. 2 to concentrate on an affected part K.

The monorail pipe 25 is formed as a hollow cylindrical member to allow a cleaning liquid to be supplied inside. The flow of the cleaning liquid supplied in this manner is bent forward to the front window 31 through a channel 33 formed in the cap 30. The liquid then flows to clean the outside of the transparent plate 32.

Figure 4A:
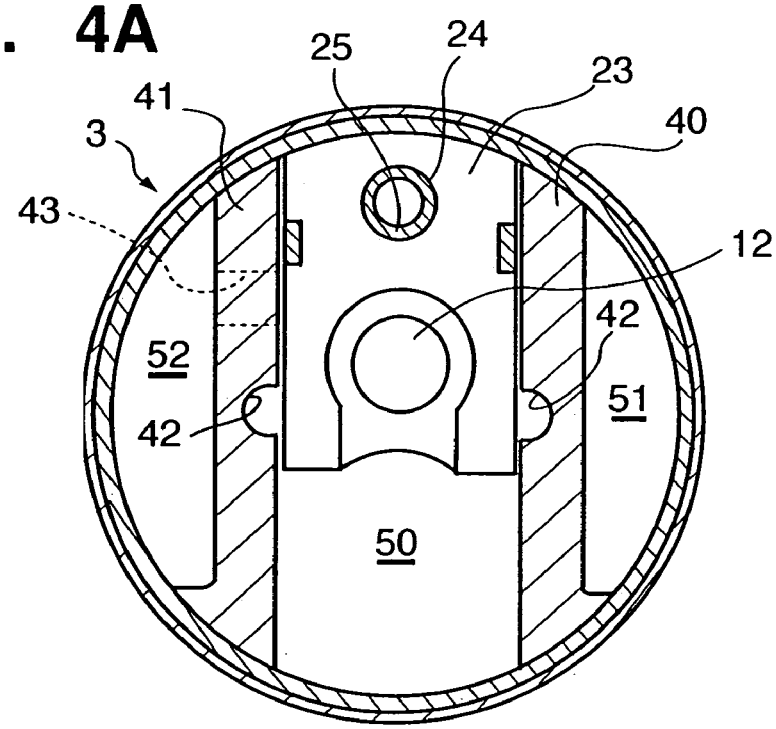
FIG. 4A is a sectional view taken along a line X—X in FIG. 2.
Figure 4B:
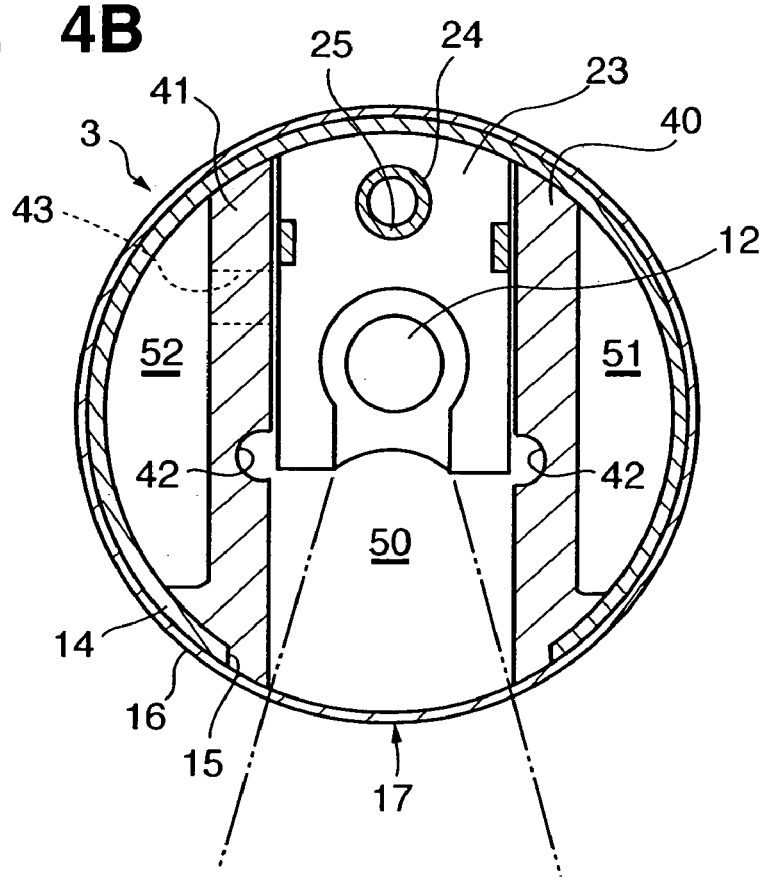
FIG. 4B is a sectional view taken along a line Y—Y in FIG. 2.

Referring to FIG. 4A, which is a sectional view taken along a line X—X in FIG. 2, and FIG. 4B, which is a sectional view taken along a line Y—Y in FIG. 2, the interior of the insertion portion 3 is partitioned by the pair of wall members 40 and 41 to form a channel chamber 50 for the injection of cooling water and a channel chamber 51 for the discharge of cooling water. Cooling water is used to cool the surface of living tissue to be irradiated with a laser beam and the overall laser irradiation mechanism 20. The channel chamber 50 is connected to the water supply tube 11 described with reference to FIG. 1. The channel chamber 51 is connected to the drain tube 10. The cooling water supplied through the water supply tube 11 flows into the channel chamber 50. The water then flows from a hole 34 near the distal end of the insertion portion 3 into the channel chamber 51, and is discharged through the drain tube 10. Part of injected cooling water also flows from a small hole 43 (see FIG. 4A) formed in the wall member 41 into a channel chamber 52. This cooling water also flows from the hole 34 into the channel chamber 51.

Circulating the cooling water in the insertion portion 3 in the above manner can improve the cooling efficiency. Although the temperature of this cooling water is not specifically limited as long as damage to the laser irradiation mechanism 20 and the irradiation surface of a living body due to irradiation with laser beams can be prevented, the temperature is preferably set to 0 to 37° C., and more preferably 8 to 25° C. at which the possibility of frostbite is low and a high cooling effect is ensured. As cooling water, a sterilized liquid, e.g., sterilized purified water or sterilized physiological saline is preferably used.

The endoscope 6 has observation fields from both the irradiation window portion 17 on a side of the insertion portion 3 and the front window 31 on the front side. This endoscope 6 therefore allows the operator to observe the surface of living tissue through the irradiation window portion 17 or front window 31 when it is irradiated with a laser beam, and also allows the operator to position the insertion portion 3 on the basis of observation through the endoscope 6 and visually check a laser irradiation position.

Referring back to FIG. 3, a slider 80 which is a locked member is fixed midway along the optical fiber 12. An engaging groove 81 is formed in the slider 80. A hook 85 serving as a lock member is locked to the engaging groove 81. A shaft member 86 is fixed to the hook 85. Power is transmitted to the shaft member 86.

Figure 5A:
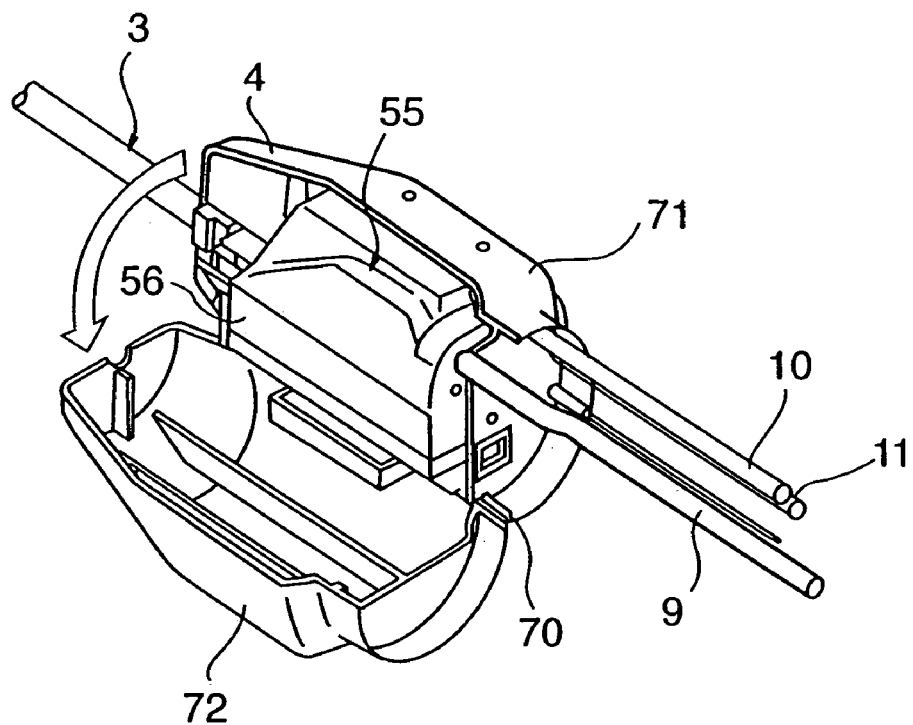
FIG. 5A is a perspective view showing a state wherein a cover portion 4 of the laser irradiation apparatus 1 is open, and a driving unit 55 is mounted in the cover portion 4.
Figure 5B:
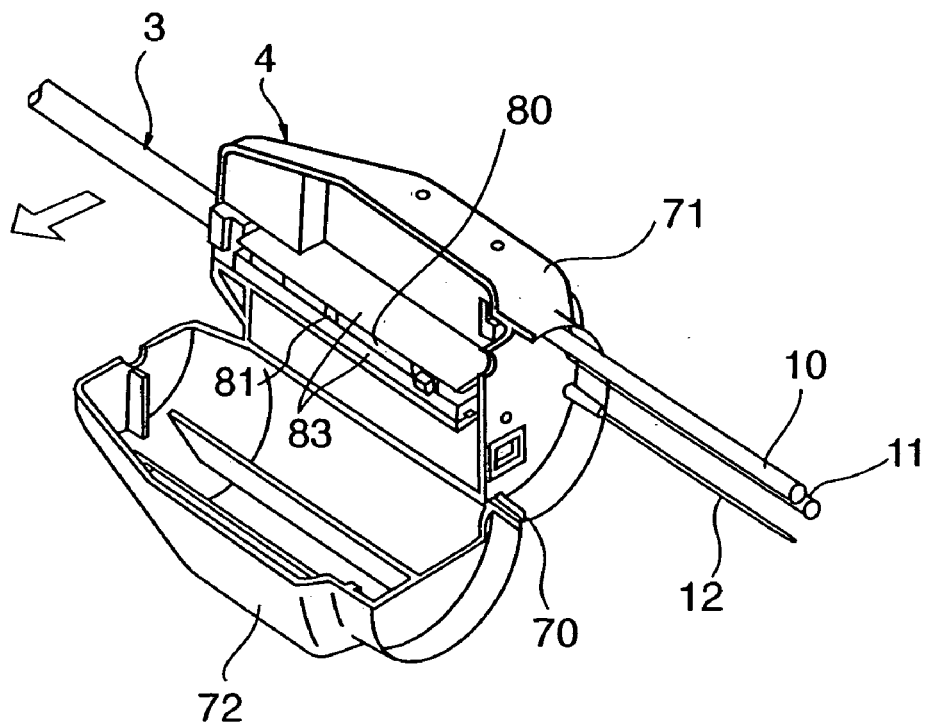
FIG. 5B is a perspective view showing a state wherein the driving unit 55 is removed.

FIG. 5A is a perspective view showing a state wherein the cover portion 4 of the laser irradiation apparatus 1 is open, and a driving unit 55 is mounted in the cover portion 4. FIG. 5B is a perspective view showing a state wherein the driving unit 55 is removed.

The same reference numerals as in FIGS. 5A and 5B denote the same parts described above, and hence a description thereof will be omitted. The driving unit 55 is detachably mounted in the cover portion 4. The driving unit 55 contains a driving mechanism (to be described later), a casing incorporating it, and the lead 9. The cover portion 4 is formed from a predetermined resin material by injection molding. The cover portion 4 includes first and second cases 71 and 72 openably connected to each other through a hinge portion 70. The driving unit 55 is stationarily held between the first and second cases 71 and 72 to be detachably housed. A pair of guide plates 83 are placed facing each other at substantially the middle portion of the first case 71, as shown in FIG. 5B. The slider 80 in the form of a thin plate shown in FIG. 3 is held in the space formed between the guide plates 83. When the hook 85 provided on the driving unit 55 is locked to the engaging groove 81 of the slider 80, the optical fiber 12 is made to slide along the axial direction of the insertion portion 3. That is, as the slider 80 reciprocates, the reciprocating motion is transmitted to the reciprocating member 23 through the optical fiber 12. Meanwhile, a laser beam is applied to the mirror 21 to be reciprocated while the tilt angle of the mirror 21 is changed in the laser irradiation mechanism 20, as described above. In this manner, the slider 80 reciprocates at a uniform velocity upon receiving reciprocating motion output from the driving unit 55.

B. Arrangement of Driving Unit

First Embodiment

Figure 6A:
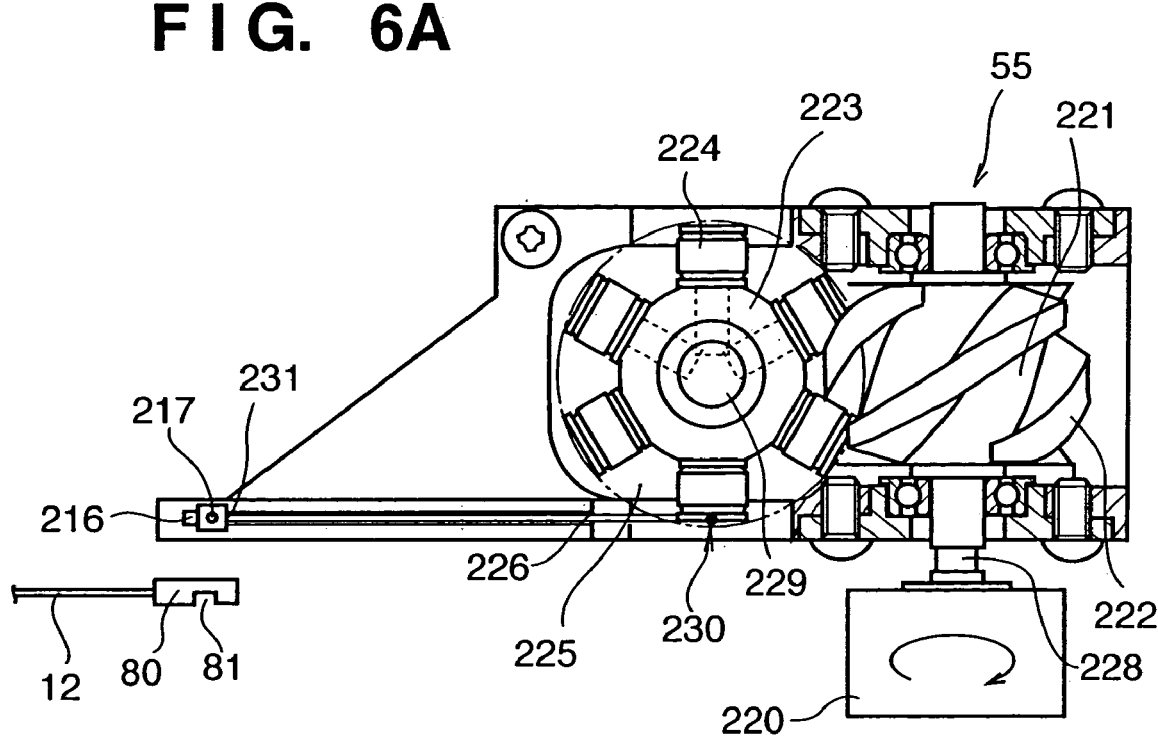
FIG. 6A is a front view showing a driving unit according to the first embodiment with a hook 85 being moved to the left.
Figure 6B:
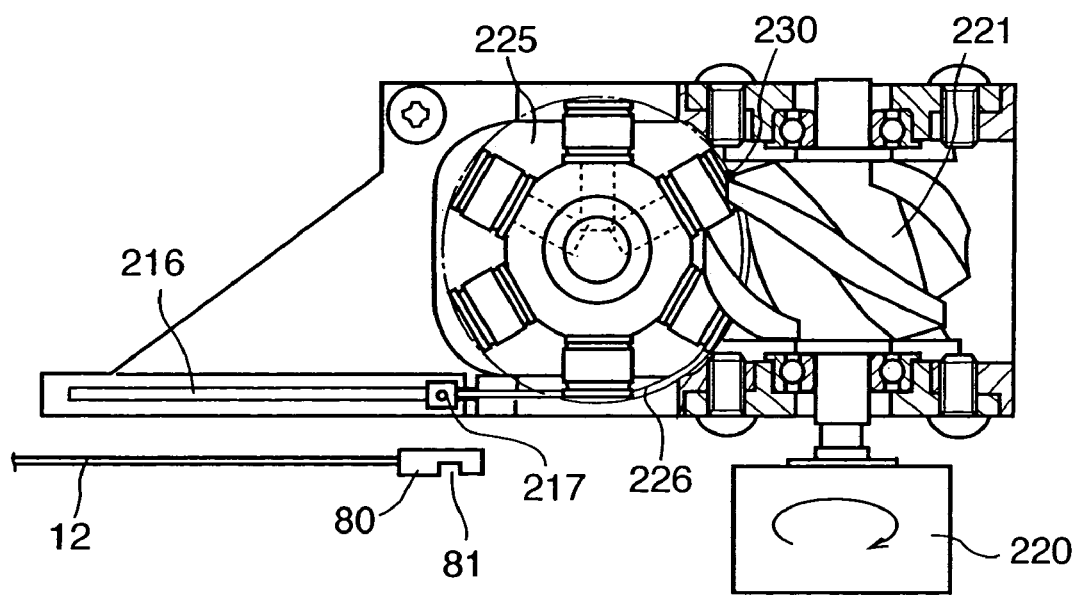
FIG. 6B is a front view showing the driving unit according to the first embodiment with the hook 85 being moved to the right.

FIG. 6A is a front view showing a driving unit according to the first embodiment after a hook 85 is moved to the left. FIG. 6B is a front view of the driving unit after the hook 85 is moved to the right. The same reference numerals as in FIGS. 6A and 6B denote the same parts described above, and a description thereof will be omitted. The reciprocal hook 85 engages with an engaging groove 81 of a slider 80 to transmit uniform reciprocating force through an optical fiber 12 in the above manner. A driving unit 55 converts uniform rotating motion from a motor 220 into uniform linear reciprocating motion. The driving unit 55 includes the motor 220 as a power source, a roller gear cam 221 having an input shaft coaxial with a motor output shaft 228, a turret 223 having a cam follower 224 in the form of a roller, and a pulley 225 having an input shaft coaxial with a turret output shaft 229.

A plurality of ribs 222 are provided for the roller gear cam 221. Motion is transmitted to the cam follower by the ribs 222. The ribs 222 are so tapered as to make the turret 223 swing at 120°. The turret 223 makes one swing per rotation of the roller gear cam 221. In order to change the direction of swinging motion, the turret 223 is temporarily decelerated and stopped, and then accelerated in the opposite direction to return to the initial velocity. The time for direction change is minimized within the range in which power transmission is free from any influence. In addition, motion other than motion for direction change becomes uniform motion. According to the above description, the turret 223 swings at 120°. Obviously, however, the present invention is not limited to this angle, and the angle can be changed depending on the length of a stroke in which a laser irradiation portion 120 is made to reciprocate or the diameter of the pulley 225.

The swinging motion of the cam follower 224 is transmitted to the pulley 225 having a rotating shaft coaxial with the cam follower 224. A wire 226 made of a flexible material is wound around the pulley 225 by a length corresponding to at least a 120° circumference. One end 230 of the wire 226 is fixed to the pulley 225 at a bonding point. The other end 231 of the wire 226 is connected to a sliding block 217 to which the hook 85 is fixed with a pin. The sliding block 217 is slidably fitted in the sliding groove 216. The swinging motion of the turret 223 is therefore converted into the uniform linear reciprocating motion of the hook 85 through the wire 226. Although the wire 226 is not limited any specific material as long as it can reliably transmit motion to the sliding block 217 without bending, the wire 226 is preferably made of a nickel/titanium shape memory alloy or the like.

As described above, in order to uniform linear reciprocating motion in the hook 85, the hook 85 is engaged with the engaging groove 81 of the slider 80 to transmit motion to the slider 80. Finally, the motion is transmitted to a laser irradiation mechanism 20 which moves while being interlocked with the slider 80. As a consequence, the rotating motion of the motor 220 is converted into the uniform linear reciprocating motion of the laser irradiation mechanism 20.

Second Embodiment

Figure 7:
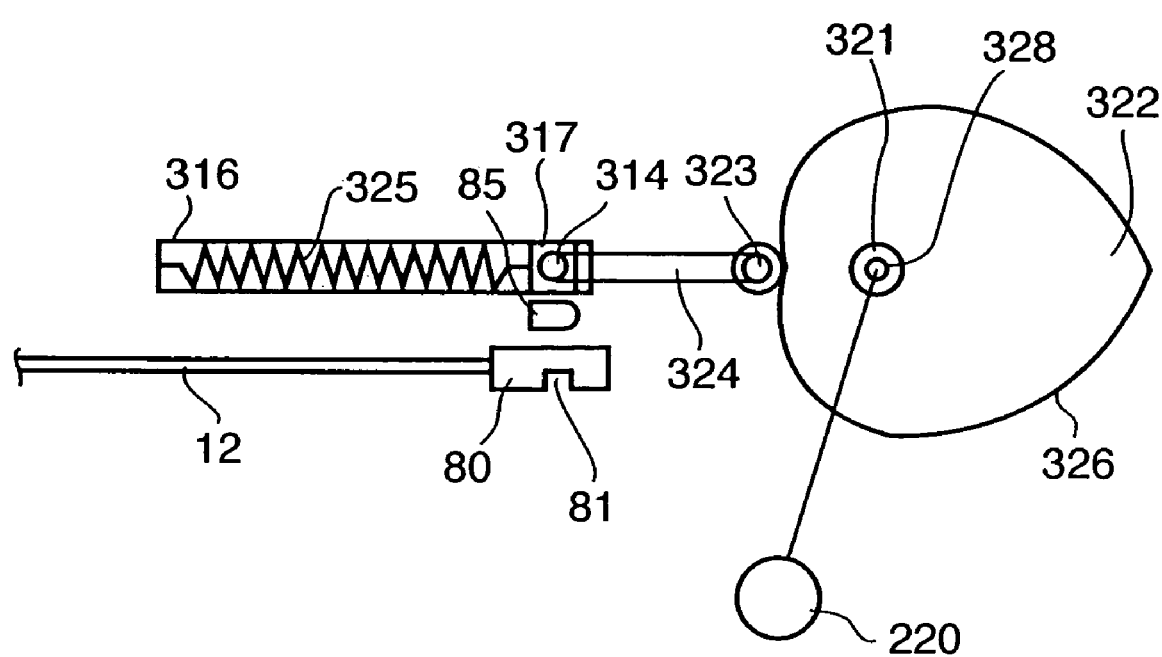
FIG. 7 is a front view showing a driving unit according to the second embodiment.

FIG. 7 is a front view showing a driving unit according to the second embodiment after a hook 85 is moved toward the proximal end of an insertion portion 3 (the right side in FIG. 7). The same reference numerals as in FIG. 7 denote the same parts described above, and a description thereof will be omitted. As shown in FIG. 7, the driving unit has a cam input shaft 321 coaxial with an output shaft 328 of a motor 220. A heart cam 322 rotates about the cam input shaft 321 as a rotation center. The heart cam 322 is in the form of a symmetrical hear-shaped plate, as shown in FIG. 7, and has a smooth, uniform cam side surface 326 on the outer surface. A cam follower 323 is placed in contact with the side surface 326 of the heart cam 322. The cam follower 323 is integrally formed, through an interlocking arm 324, with a sliding block 317 fixed to the hook 85 with a pin 314. Therefore, the hook 85 always moves while being interlocked with the cam follower 323. The hook 85 engages with an engaging groove 81 of a slider 80 to reliably transmit the motion of the hook 85 to the slider 80. The sliding block 317 is slidably fitted in a sliding groove 316, and is always receiving force that make the heart cam 322 and cam follower 323 come into contact with each other through a spring 325. This makes it possible to always bring the cam follower 323 into contact with the side surface 326 of the heart cam 322.

With the above arrangement, the heart cam 322 makes one rotation per rotation of the motor 220, and the cam follower 323 follows the rotating motion of the heart cam 322 to make one uniform linear reciprocating motion along the side surface 326. That is, as the hook 85 integrally formed with the cam follower 323 makes similar motion, the motion is transmitted to the slider 80. Since the slider 80 moves while being interlocked with a laser irradiation portion 20, the laser irradiation portion 20 makes uniform linear reciprocating motion. As described above, since the rotating motion of the motor is directly converted into uniform linear reciprocating motion without the mediacy of swinging motion. This makes it possible to realize a compact, lightweight driving mechanism and a reduction in cost owing to a reduction in the number of parts.

Third Embodiment

Figure 8:
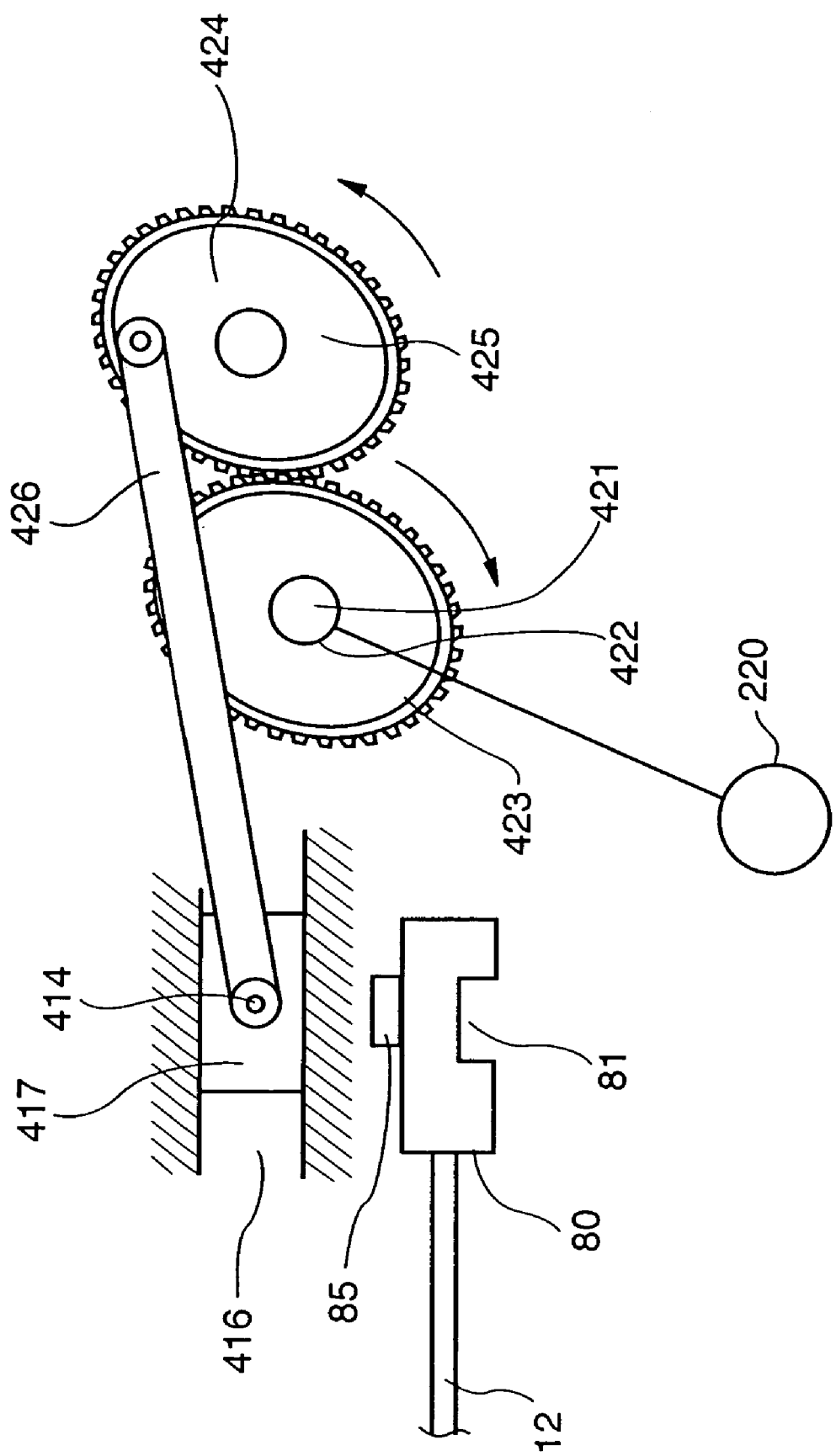
FIG. 8 is a front view showing a driving unit according to the third embodiment.

FIG. 8 is a front view showing a driving unit according to the third embodiment after a hook 85 is moved to some midway position. The same reference numerals as in FIG. 8 denote the same parts described above, and a description thereof will be omitted. A first elliptic gear 423 rotates about an input shaft 422 as a rotation center which is coaxial with an output shaft 421 of a motor 220. A second elliptic gear 425 is placed to mesh with a gear on the circumference of the first elliptic gear 423. The second elliptic gear 425 rotates about a shaft 424, and a crank arm 426 is coupled to the second elliptic gear 425 in the same plane as the shaft 424. The crank arm 426 is integrally formed with a sliding block 417 fixed to the slide 85 with a pin 414. The sliding block 417 is slidably fitted in a sliding groove 416. Therefore, the slide 85 moves while being interlocked with the crank arm 426. The slide 85 engages with an engaging groove 81 of a slider 80 to reliably transmit the motion of the slide 85 to the slider 80.

Referring to FIG. 8, when the sliding block 417 is located nearest to the base portion of an insertion portion 3, the major axis of the first elliptic gear 423 meshes with the minor axis of the second elliptic gear 425. With this structure, the sliding block 417 makes linear reciprocating motion with a constant velocity. This motion is transmitted to a laser irradiation portion 20 through the slide 85 and slider 80. As a result, the laser irradiation portion 20 makes linear reciprocating motion with a constant velocity.

Fourth Embodiment

Figure 9:
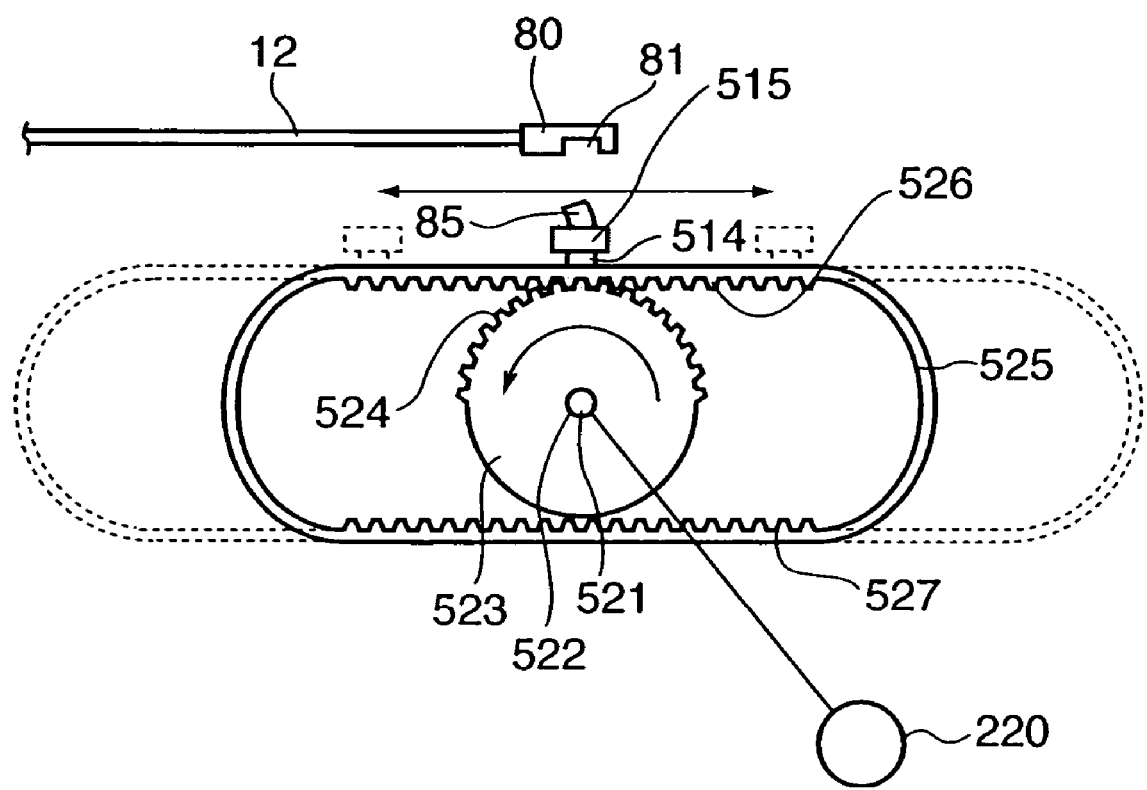
FIG. 9 is a front view showing a driving unit according to the fourth embodiment.

FIG. 9 is a schematic view for explaining the arrangement of the fourth embodiment. The same reference numerals as in FIG. 9 denote the same parts described above, and a description thereof will be omitted. A half gear 523 having a sector gear 524 rotates about an input shaft 522 as a rotation center which is coaxial with an output shaft 521 of a motor 220 in the direction indicated by the arrow. Note that the motor 220 and half gear 523 are fixed to a casing (not shown) of a driving unit 55. An oval sliding member 525 is movably placed to mesh with the half gear 523 at two points on its circumference. First and second gear portions 526 and 527 are formed on the inside linear portions of the sliding member 525 so as to oppose each other. The sliding member 525 moves to right and left only when these gear portions mesh with the sector gear 524 of the half gear 523. As a motor 220 rotates, therefore, the half gear 523 rotates in one direction, and the sliding member 525 continuously moves to right and left, alternately, only when the sector gear 524 meshes with the first gear portion 526 and second gear portion 527 of the sliding member 525. As a consequence, the sliding member 525 makes linear reciprocating motion with a constant velocity.

A sliding block 515 and slide 85 are fixed to an outside middle portion of the sliding member 525 with a pin 514. The hook 85 engages with an engaging groove 81 of a slider 80. This makes it possible to reliably transmit the motion of the hook 85 to the slider 80. In this case, since the hook 85 moves while being interlocked with the sliding member 525, the hook 85 makes linear reciprocating motion with a constant velocity, and transfers power to a laser irradiation portion 20 through the slider 80. As a consequence, the laser irradiation portion 20 makes linear reciprocating motion with a constant velocity.

Fifth Embodiment

Figure 10A:
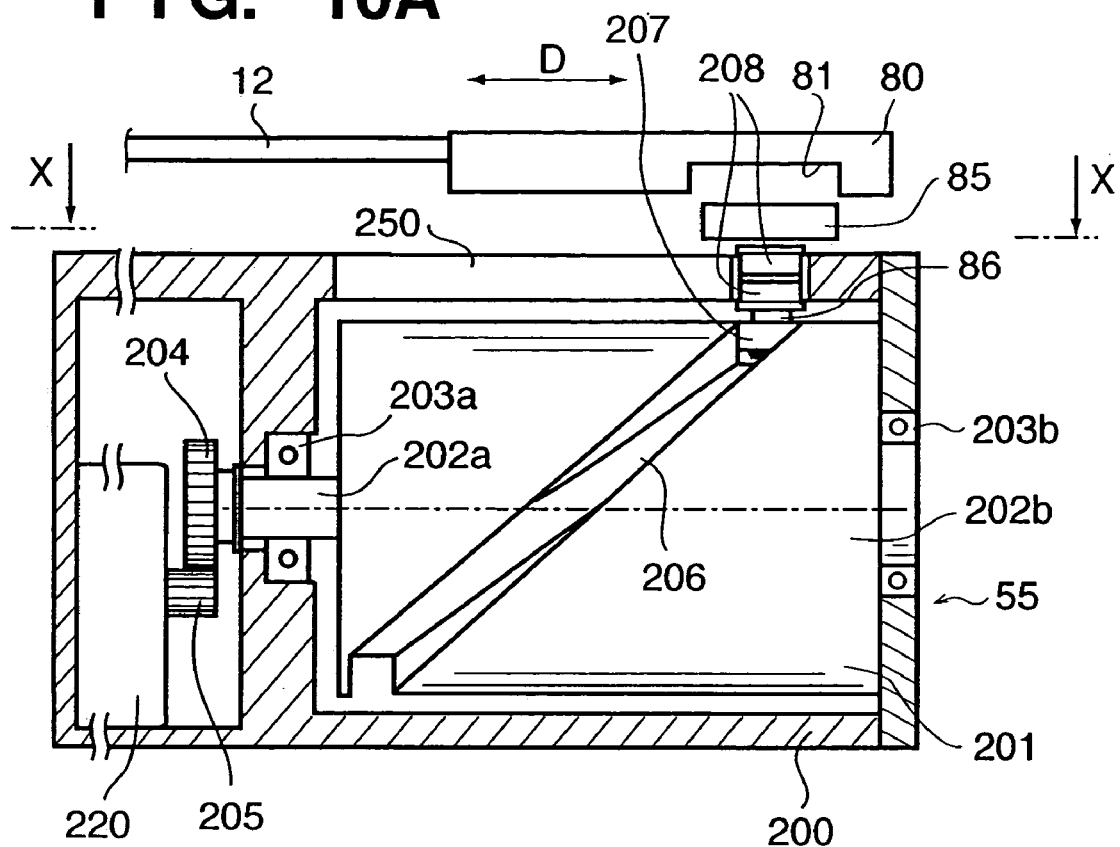
FIG. 10A is a partially cutaway plan view showing a driving unit 55 according to the fifth embodiment with a hook 85 being moved to the right.
Figure 10B:
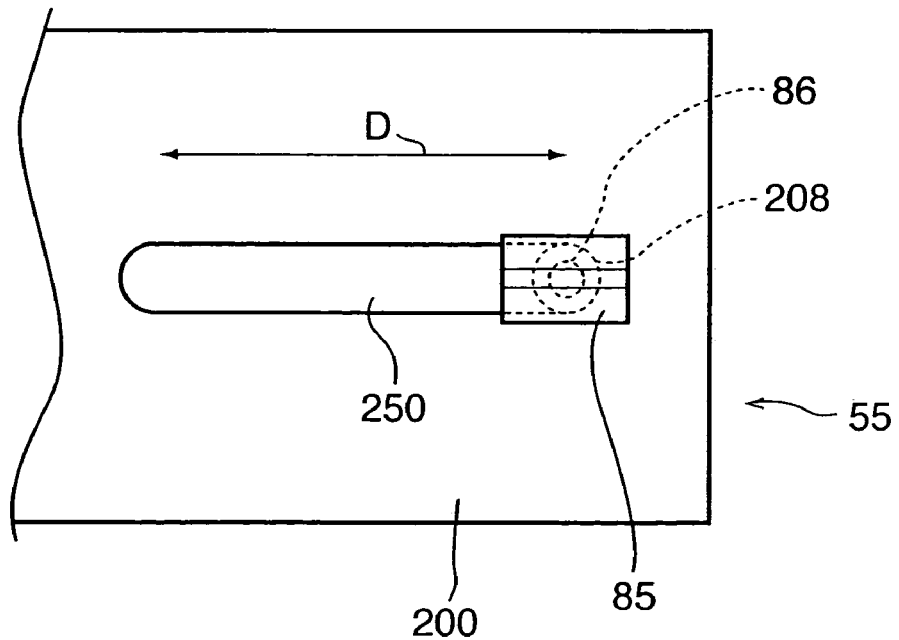
FIG. 10B is a sectional view taken along a line X—X in FIG. 10A.

FIG. 10A is a front view showing a driving unit 55 according to the fifth embodiment after a hook 85 is moved toward the proximal end of an insertion portion 3 (the right side in FIG. 10A). FIG. 10B is a sectional view taken along a line X—X in FIG. 10A. The same reference numerals as in FIGS. 10A and 10B denote the same parts described above, and a description thereof will be omitted. The reciprocal hook 85 engages with an engaging groove 81 of a slider 80 to transmit the power of reciprocating motion with a constant velocity through an optical fiber 12 in the above manner.

The driving unit 55 converts uniform rotating motion from a motor 220, which rotates at a constant velocity, into reciprocating motion with a constant velocity. The driving unit 55 incorporates the motor 220 as a power source in a base portion 200, and has a gear 205 fixed to the output shaft of the motor 220. A cylindrical member 201 has shaft portions 202a and 202b formed from two ends serving as a rotational center axis. The shaft portions 202a and 202b are axially supported by bearings 203a and 203b fixed to the base portion 200. With this structure, the cylindrical member 201 is held to be rotatable about an axis parallel to the axis of the insertion portion 3 in the longitudinal direction. A gear 204 which meshes with the gear 205 is fixed to one of the shaft portions 202a and 202b.

An endless groove portion 206 is formed in the outer surface of the cylindrical member 201. The endless groove portion 206 reciprocates/drives the hook 85 locked to the slider 80 at a constant velocity and minimizes the time for direction change.

The hook 85 is fixed to a shaft member 86 in the above manner. A roller 207 and a pair of flanged radial ball bearings 208 are pivotally provided on the shaft member 86. The roller 207 enters the endless groove portion 206. In the base portion 200, the radial ball bearings 208 are set in a guide groove 250 formed along the reciprocating direction of the slider 80 so as to be prevented from dropping.

Figure 11:
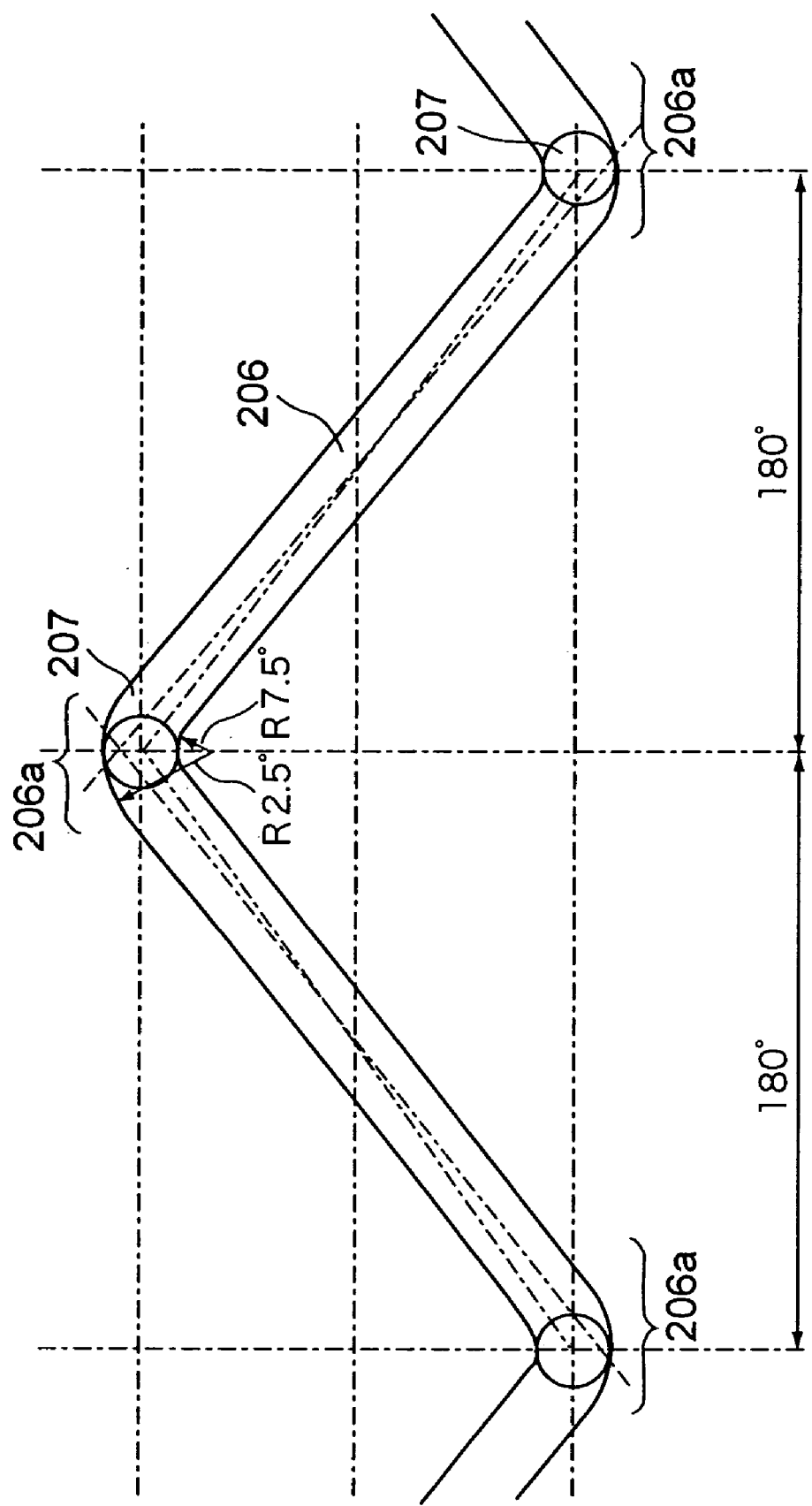
FIG. 11 is a developed view showing an endless groove portion 206 formed in the outer surface of a cylindrical member 201 with the groove portion being developed 360°.

FIG. 11 is a developed view showing the endless groove portion 206 formed in the outer surface of the cylindrical member 201 with the groove portion being developed 360°. As shown in FIG. 11, the endless groove portion 206 makes the hook 85 be reciprocated/driven at a constant velocity along the linear portions of the angular shape, and a plurality of bent portions 206a for minimizing the time for direction change of the hook 85 are formed at a peak point and valley points of the angular shape, as shown in FIG. 11.

According to the driving unit 55 described above, when the motor 220 is energized, constant rotating motion is transmitted to the cylindrical member 201 through the gears. As a consequence, the hook 85 reciprocates once in the guide groove 250 per rotation of the cylindrical member 201. In order to change the direction of this reciprocating motion, the hook 85 is decelerated and stopped, and then accelerated in the opposite direction. The time for direction change is minimized from the bent portions 206a of the endless groove portion 206. According to the above arrangement, since the motor 220 and cylindrical member 201 can be arranged in a line, the size in the radial direction can be reduced.

Sixth Embodiment

Figure 12A:
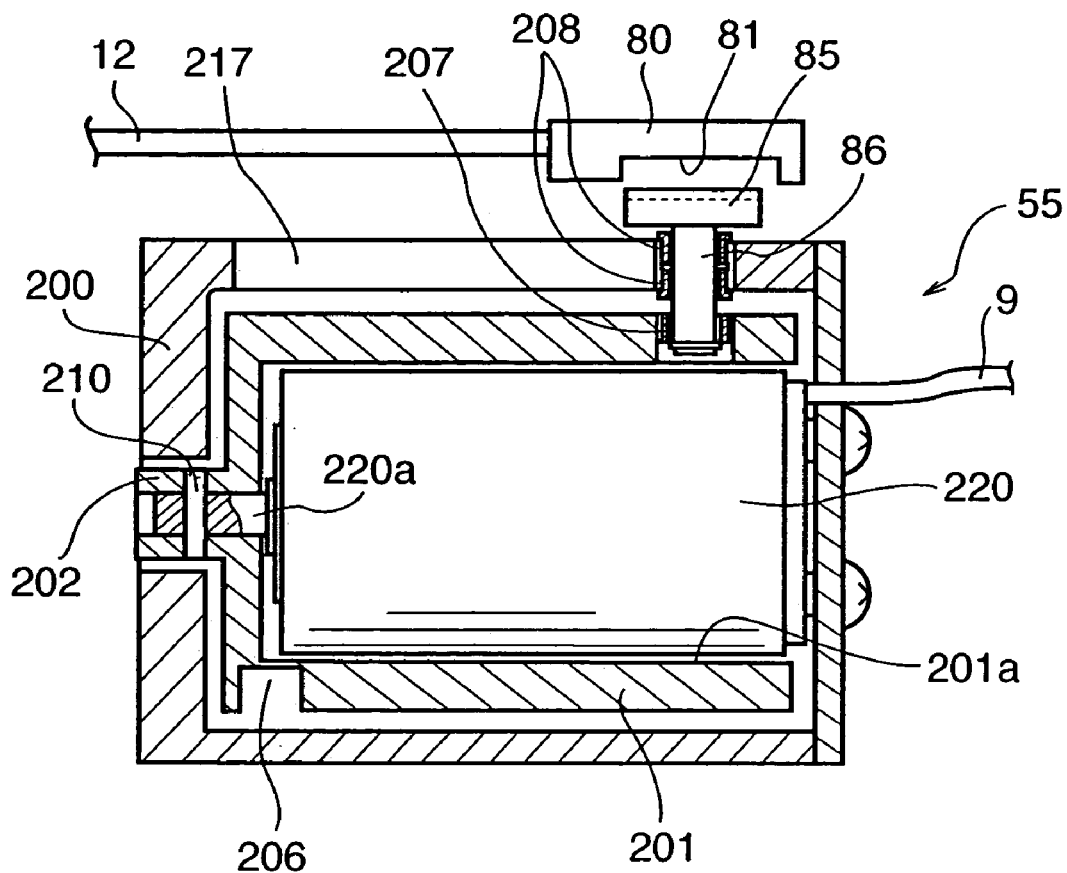
FIG. 12A is a partially cutaway front view of a cylindrical member 201.
Figure 12B:
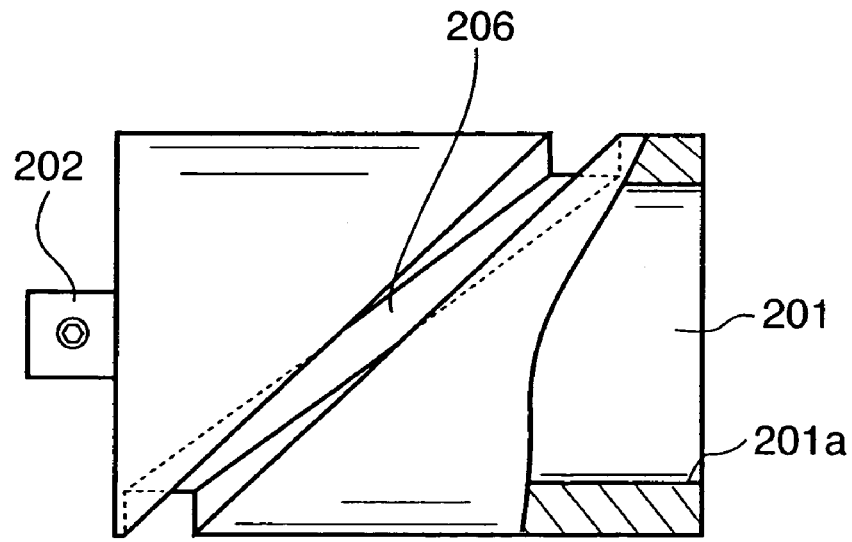
FIG. 12B is a central sectional view showing a driving unit 55 according to the sixth embodiment after a hook 85 is moved to the right.

FIG. 12A is a central sectional view showing a driving unit 55 according to the sixth embodiment after a hook 85 is moved toward the proximal end of an insertion portion 3 (the right side in FIG. 12A). FIG. 12B is a partially cutaway front view of a cylindrical member 201. The same reference numerals as in FIGS. 12A and 12B denote the same parts described above, and a description thereof will be omitted. A reciprocal hook 85 engages with an engaging groove 81 of a slider 80 and transmits the power of uniform reciprocating motion through an optical fiber 12. The cylindrical member 201 has an endless groove portion 206 formed on the outer surface, and is prepared as a hat-like member having a hollow portion 201a, as shown in FIGS. 12A and 12B. A shaft portion 202 is provided on only one end of the cylindrical member 201.

A motor 220 is fixed to a lid portion fixed to a base portion 200, and hence can be mounted on the base portion 200. In addition, since the motor 220 has an outer diameter equal to or less than the inner diameter of the hollow portion 201a, the motor 220 can be incorporated in the cylindrical member 201, as shown in FIG. 12B, and the shaft portion 202 described above is fixed to a motor output shaft 220a by press-fitting a pin 210.

According to the driving unit 55 of the sixth embodiment described above, since the motor 220 and cylindrical member 201 are arranged in the coaxial direction, a reduction in size can be achieved along the moving direction of the hook 85.

Seventh Embodiment

FIG. 13 is a developed view showing an endless groove portion 206 formed in the outer surface of the cylindrical member of a driving unit 55 according to the seventh embodiment with the groove portion being developed 360°.

As shown in FIG. 13, the endless groove portion 206 makes a hook 85 be reciprocated/driven at a uniform velocity along the linear portions of the angular shape, and a plurality of shaped portions 206a for minimizing the time for direction change of the hook 85 are formed at peak points and valley points of the angular shape. According to the above arrangement, as a cylindrical member 201 is driven clockwise by a motor 220, a roller 207 held on a shaft member 86 of the hook 85 moves in the direction indicated by an arrow D1 in FIG. 13. After the direction of the roller 207 is changed by the shaped portion 206a, the roller 207 moves in the direction indicated by an arrow D2 in FIG. 13. Thereafter, the roller 207 moves forward in the direction indicated by an arrow D3, and moves in the direction indicated by an arrow D4 to return to the initial position again. Every time the cylindrical member 201 makes one rotation, therefore, the hook 85 can be reciprocated/driven twice.

In the above manner, when the hook 85 is linearly reciprocated/driven at a uniform velocity and engaged with an engaging groove 81 of a slider 80, the reciprocating motion transmitted to the slider 80 is finally transmitted to a laser irradiation portion 20. In this manner, the uniform rotating motion of the motor 220 is converted into the uniform linear reciprocating motion of the laser irradiation portion 20.

When heating treatment like that describe above is to be performed, the laser irradiation portion 20 is reciprocated/driven in the axial direction at a period of 1 to 10 Hz, and preferably 1 to 6 Hz. As a laser beam applied to living tissue, divergent light, parallel light, or convergent light can be used. In order to convert a laser beam into convergent light, an optical system for converting a laser beam into convergent light may be placed midway along the laser optical path. A laser beam to be used is not specifically limited as long as it has deep transmission capability against living tissue. However, a laser beam to be used preferably has a wavelength of about 750 to 1,300 nm, or about 1,600 to 1,800 nm, because a laser beam having such a wavelength exhibits excellent deep transmission capability against living tissue, in particular. A laser source device 101 which generates a laser beam in the above wavelength range includes, for example, a gas laser such as an He-Ne laser, a solid-state laser such as an Nd-YAG laser, and a semiconductor laser such as a GaAlAs laser.

Eighth Embodiment

Figure 14:
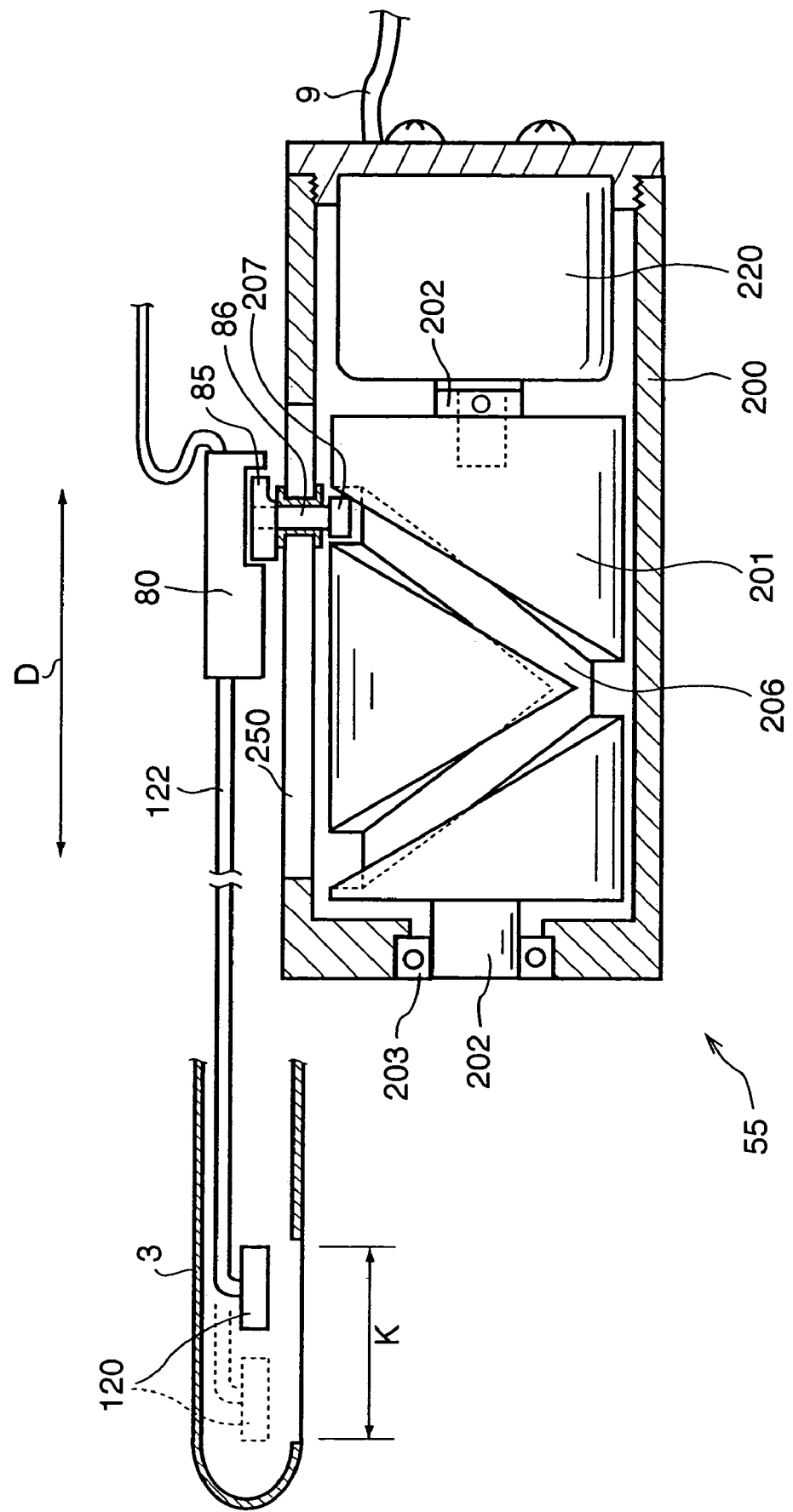
FIG. 14 is a sectional view of the main part of the eighth embodiment, showing a case wherein an ultrasonic radiator 120 is provided as an energy irradiation portion.
Figure 15:
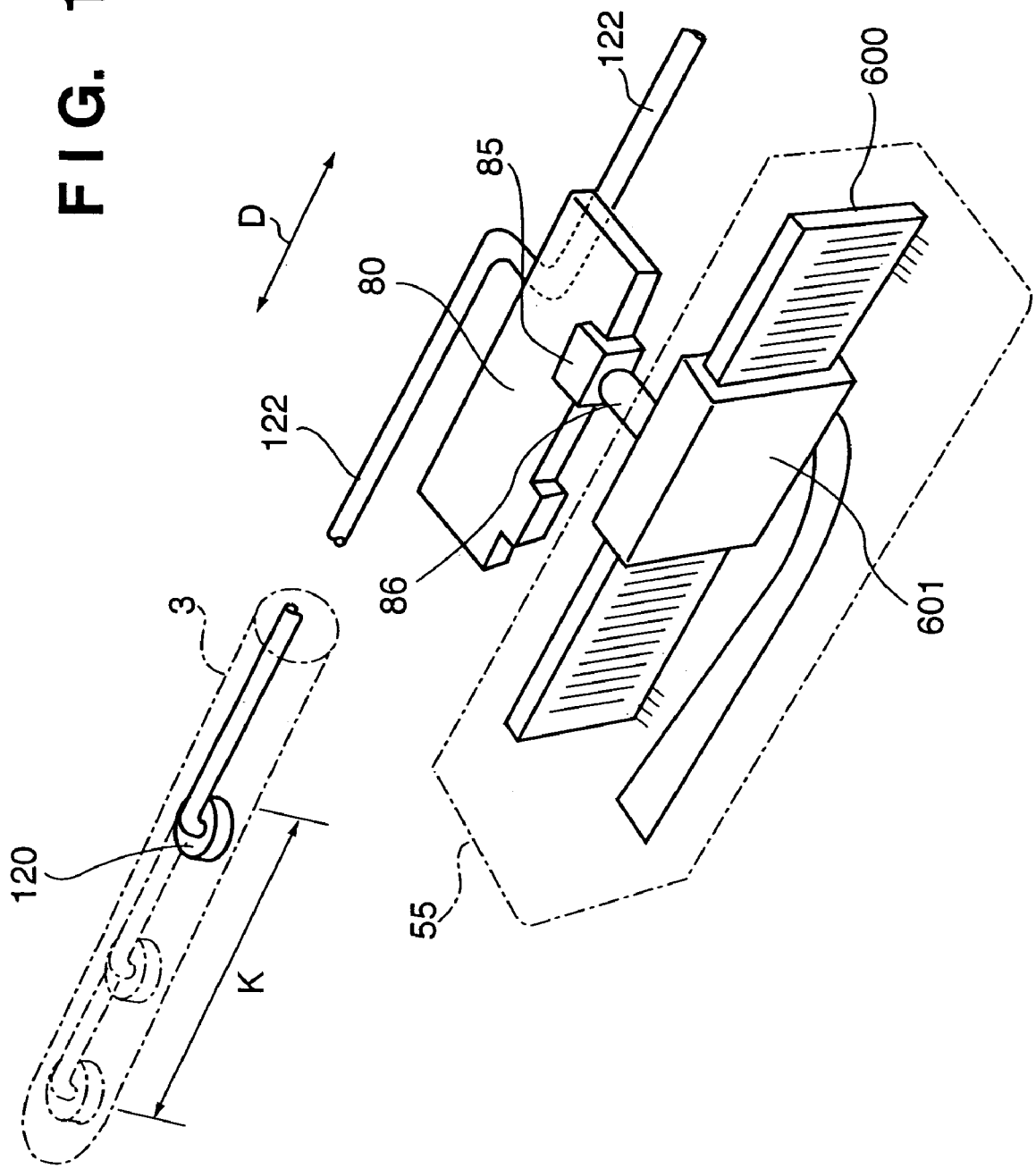
FIG. 15 is a perspective view showing the outer appearance of another form of the energy irradiation apparatus according to the eighth embodiment in FIG. 14.

FIGS. 14 and 15 are sectional views each showing the main part of the eighth embodiment in which an ultrasonic radiator 120 is provided as an energy irradiation portion. The same reference numerals as in FIGS. 14 and 15 denote the same parts described above, and a description thereof will be omitted. The ultrasonic radiator 120 which generates ultrasonic waves when being energized through a lead 122 is provided in an insertion portion 3 so as to be reciprocal between the positions indicated by the solid and broken lines in FIG. 14. With this arrangement, an affected part K is irradiated with ultrasonic waves. A slider 80 is fixed to the lead 122. The slider 80 engages with a hook 85 to be reciprocated/driven at a uniform velocity in the direction indicated by an arrow D. A shaft member 86 is fixed to the hook 85. A roller 207 is located in an endless groove portion 206. A shaft portion 202 is fixed to a cylindrical member 201 on the right side with respect to the output shaft of a motor 220. The shaft portion 202 on the left side is axially supported by a bearing 203 fixed to a base portion 200.

As shown in FIG. 15, the hook 85 may be fixed to a moving part 601 of the linear motor through the shaft member 86. The moving part 601 is designed to be reciprocated in the longitudinal direction of a stator 600 by energization with a predetermined polarity.

According to the above arrangement, when the hook 85 reciprocates at a constant velocity (FIG. 14) and a moving part 610 reaches a constant reciprocating velocity from a stopped state (FIG. 15), a region on the surface of living tissue can be irradiated with uniform ultrasonic waves by energizing the ultrasonic radiator 120. In this case, even if the time for direction change is somewhat long at the two ends, a given region can be irradiated with energy when the moving part reaches uniform linear reciprocating motion. Therefore, this arrangement is suitable for energy irradiation on a surface layer.

C. Comparison with Conventional Driving Unit

Figure 16:
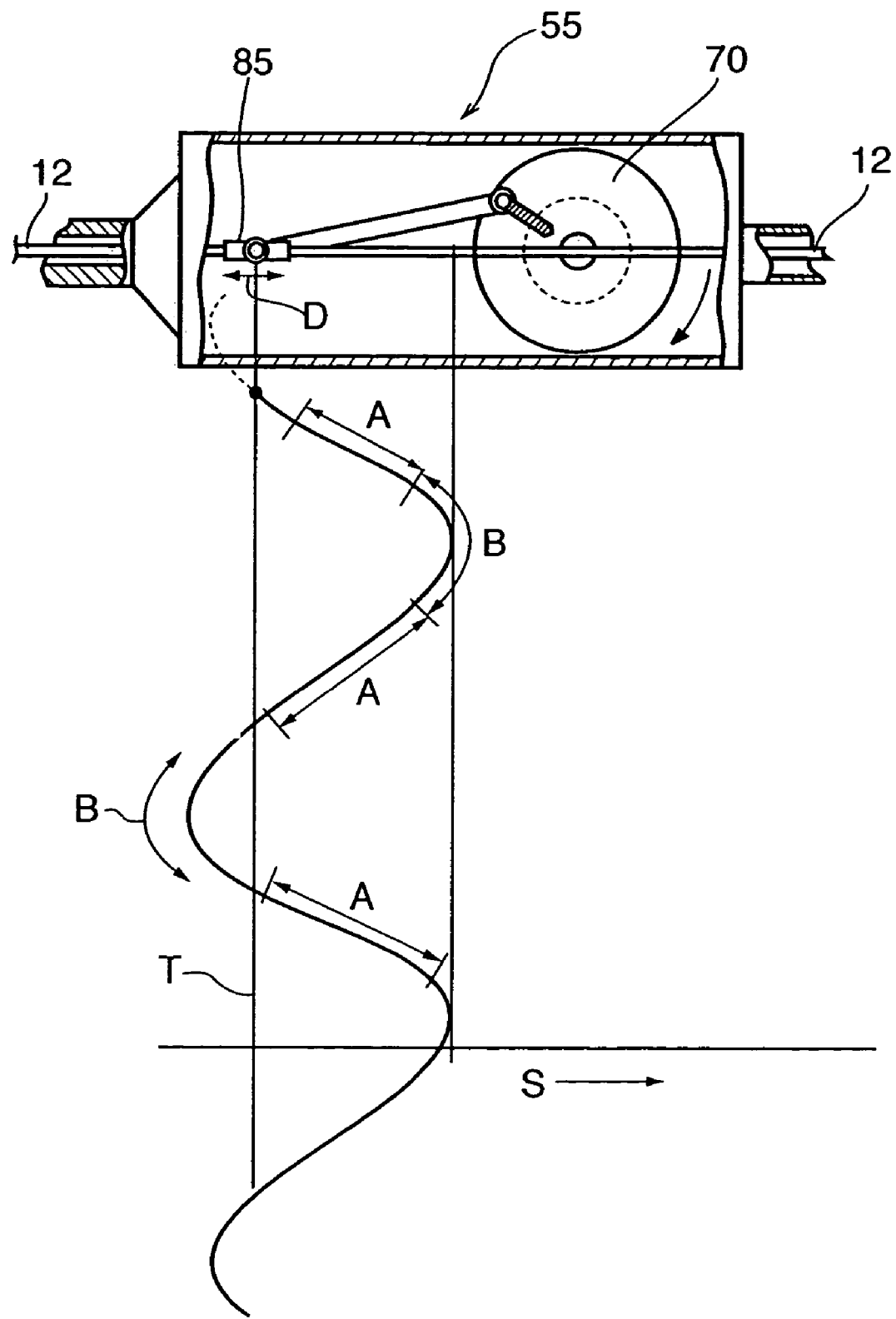
FIG. 16 is a view for explaining the crank mechanism of a conventional driving unit used for comparison with the present invention.

FIG. 16 is a view showing the schematic arrangement of a conventional driving unit 55 which makes linear reciprocating motion for the sake of comparison. Referring to FIG. 16, linear reciprocating motion is driven by a crank mechanism including a link having one end pivotally/axially supported on a motor-driven disk 70 and the other end pivotally/axially supported on a slide 85. With this structure, reciprocating motion produces a sine curve, and hence the moving velocity always changes. The time for direction change at two end portions B becomes longer than at an intermediate portion A. In addition, it is difficult to make motion symmetric about the center of reciprocating motion. The time for direction change therefore tends to be longer at an end on the base portion side of the insertion portion 3. Referring to FIG. 16, reference symbol T denotes the time axis; and S, the axis representing the position of the slide 85.

Figure 17:
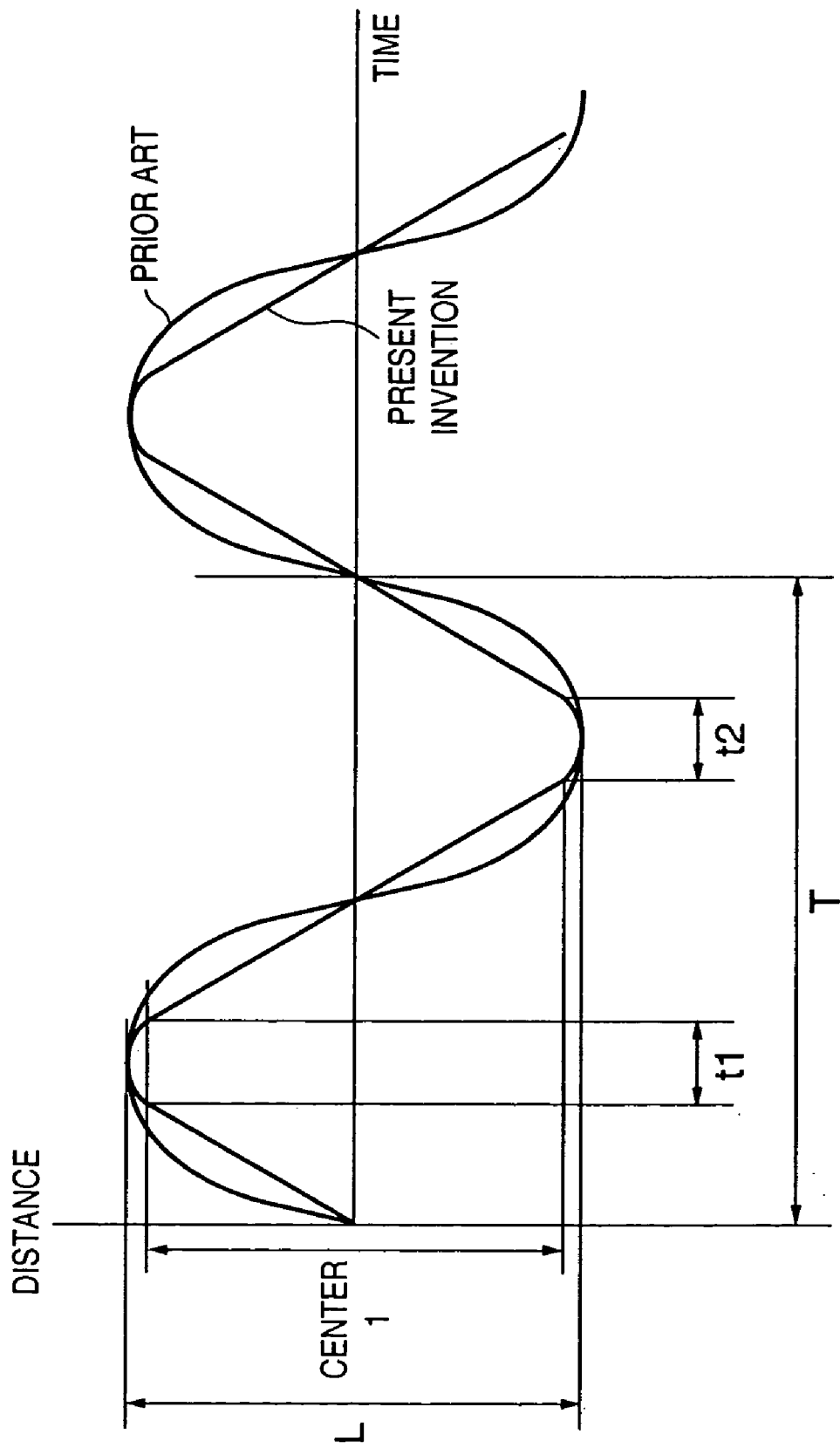
FIG. 17 is a graph for explaining comparison between the operation of the driving unit of the present invention and that shown in FIG. 16.

FIG. 17 shows a comparison between driving units according to the present invention and prior art, with the ordinate representing the position (distance); and the abscissa, the time. Referring to FIG. 17, reference symbol L denotes the total length of a reciprocating motion stroke; l, the length of a uniform movement interval; and t1 and t2, the times for direction change which are required to change the direction of motion at two end portions in the present invention.

The present invention is characterized in that a ratio X of the length l of a uniform reciprocating motion interval to the total length L of a reciprocating motion stroke is high, and a ratio Y of the time of direction change (t1+t2) to the stroke time T of reciprocating motion is low. In this case, X and Y are represented by $$X(\%) = (l/L) \times 100$$

$$Y(\%) = ((t1+t2)/T) \times 100$$

In this case, the value of X is preferably 70 (%) or more, and the value Y is preferably 35 (%) or less. More preferably, X=74.8 to 81, and Y=27.8 to 33.3. In the structure according to the first embodiment, if X exceeds 81 or Y becomes smaller than 27.8, a trouble may occur in the movement of the cam.

Figure 18:
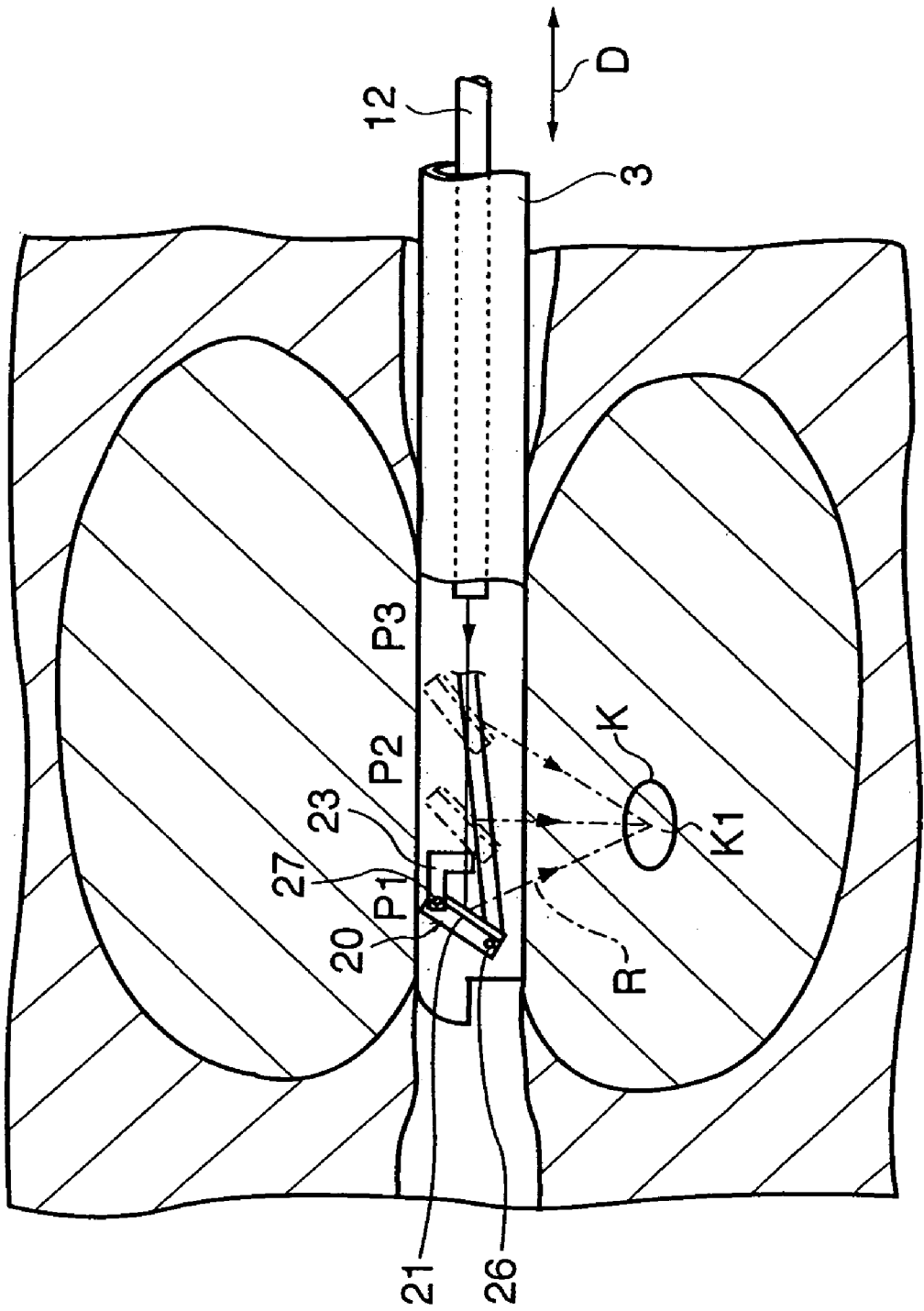
FIG. 18 is a view for explaining the operation of inserting the insertion portion 3 into a lumen to treat an affected part of a living body.

In contrast to this, referring to FIG. 18, which schematically shows laser optical paths when a laser irradiation portion 20 is located at a distal end position P1, intermediate position P2, and proximal end position P3 in reciprocating motion, when the laser irradiation portion 20 is located at the distal end position P1, the laser irradiation portion 20 stands almost perpendicular to the axial direction of the insertion portion 3 and reflects a laser beam at a small reflection angle. When the laser irradiation portion 20 is located at the proximal end position P3, the laser irradiation portion 20 tilts almost parallel to the axial direction of the insertion portion 3 and reflects a laser beam at a large reflection angle. For this reason, when a mirror 21 of the laser irradiation portion 20 reciprocates while changing its tilt angle, although the exit position of a laser beam always moves, the optical axis of a laser beam is always concentrated on a target point K1 inside a target region K as a region to be heated. In addition, a laser beam is continuously applied to only the target point K1, and is intermittently applied to other living tissues such as a surface layer. Therefore, the target point K1 is heated by the applied laser beam to reach a desired temperature. Other living tissues such as a surface layer receive a laser beam for a short period of time, and are cooled by cooling water. Such tissues are therefore hardly heated, generating only a small amount of heat.

D. Stabilization of Curative Effect

Figure 19A:
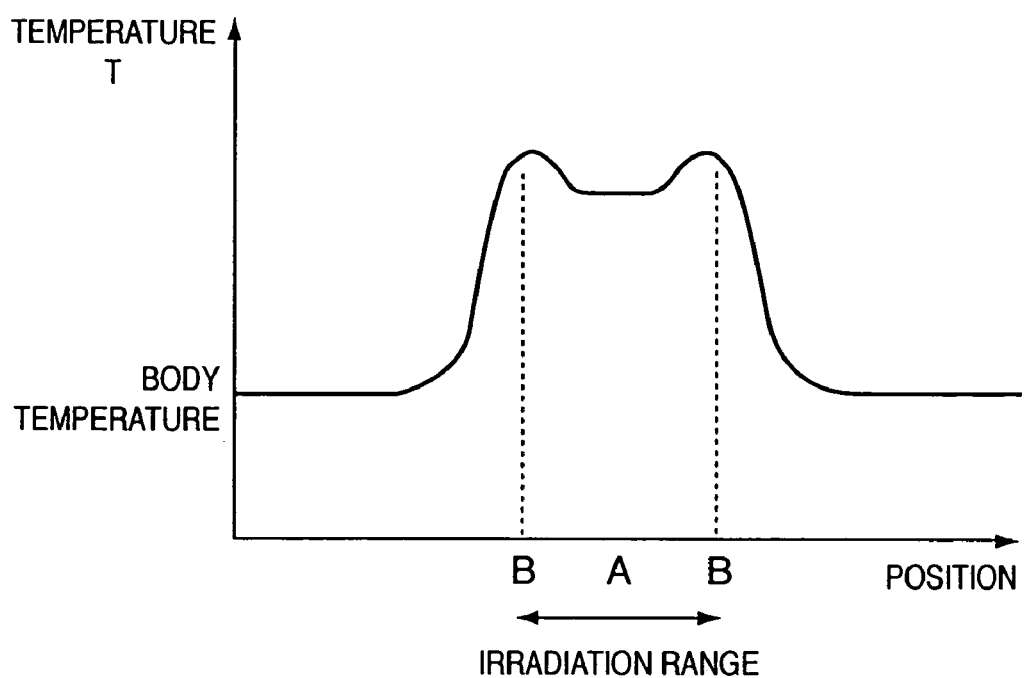
FIG. 19A is a graph showing a temperature distribution obtained by a conventional laser irradiation apparatus.
Figure 19B:
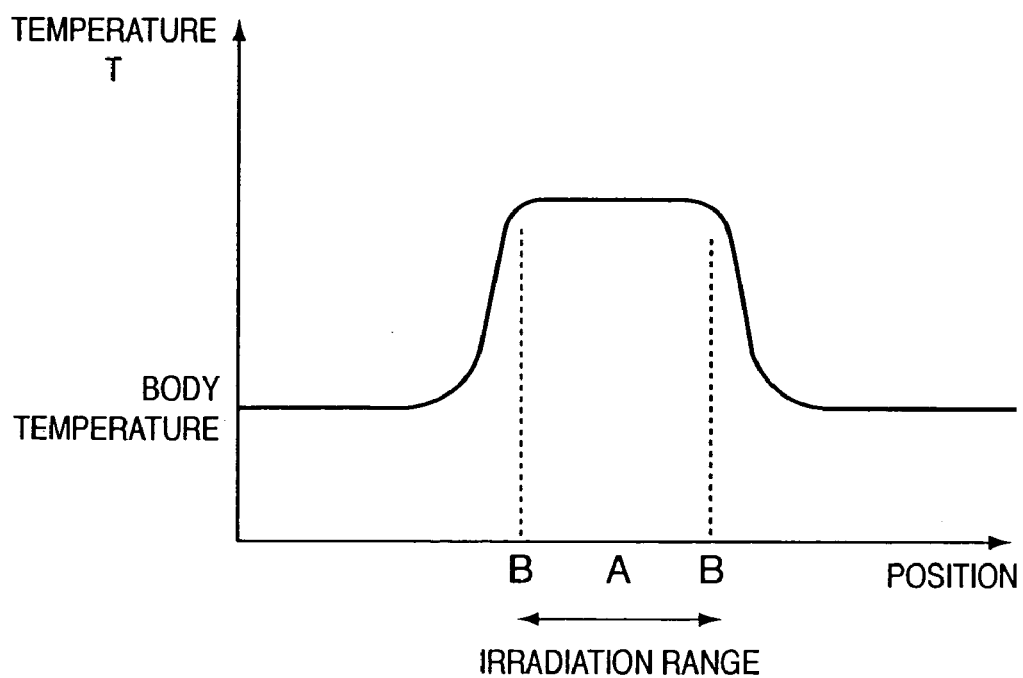
FIG. 19B is a graph showing a temperature distribution obtained by a laser irradiation apparatus according to the present invention.

FIGS. 19A and 19B are graphs each schematically showing how a temperature distribution appears around surface layer tissue which is brought into tight contact with an irradiation window portion 17. In order to help understanding of the difference between the prior art and the present invention, each drawing is plotted in the absence of the influences of the circulation of cooling water and the like.

FIG. 19A shows the temperature distribution obtained by reciprocating motion at an angular velocity in the prior art. As shown in FIG. 19A, since the time for direction change is long in regions B corresponding to the two end portions of reciprocating motion, tissue is locally heated, and hence it may become more difficult to preserve the surface layer tissue.

FIG. 19B shows the temperature distribution obtained by constant reciprocating motion in the present invention. As shown in FIG. 19B, the time for direction change is minimized at the two ends of reciprocating motion of the laser irradiation portion 20 according to each embodiment of the present invention, as described above. Since the time for direction change at the two ends becomes shorter, no local heat generation occurs at the two ends, and irradiation energy is reliably dispersed on the surface layer. This makes it possible to efficiently concentrate light on a central portion to heat it mostly strongly. This can cause heating/necrosis of only deep lesion while preserving surface layer tissue, thus stabilizing a curative effect.

As has been described above, according to the present invention, since the time for direction change becomes shorter at two ends, and constant linear reciprocating motion is made, irradiation energy is reliably dispersed on a surface layer, and light is efficiently concentrated on a central portion to heat it most strongly. This makes it possible to cause heating/necrosis of only deep lesion while preserving surface layer tissue, thus stabilizing a curative effect. Even if normal tissue such as urethra or rectum is present near the prostate as in the case of a prostate ailment such as benign prostatic hyperplasia or prostatic cancer, in particular, heating treatment can be effectively applied to only the inside of the prostate. This makes it possible to make ideal treatment. This allows to properly cope with variations in the depth of a deep portion by changing the tilt angle range of the mirror 21 as needed.

Note that the embodiments described above do not limit the present invention, and can be variously changed by the person skilled in the art within the technical idea of the present invention.

As has been described above, according to the present invention, an energy irradiation apparatus can be provided, which can uniformly irradiate a lesion with energy without locally concentrating energy.

In addition, an energy irradiation apparatus can be provided, which can preserve living tissue of a normal surface layer by uniformly irradiating only a deep portion of a lesion of living tissue with energy.

The present invention is not limited to the above embodiments and various changes and modifications can be made within the spirit and scope of the present invention. Therefore, to apprise the public of the scope of the present invention, the following claims are made.

What is claimed is:

1. An energy irradiation apparatus comprising an insertion portion which includes a hollow cylindrical member having a sealed distal end portion and is configured to be inserted into a living body, and an energy irradiation mechanism which is placed inside the hollow cylindrical member and radiates energy to living tissue through an irradiation window portion which is provided on a side wall of the hollow cylindrical member to extend in a longitudinal direction, wherein said energy irradiation mechanism comprises an energy irradiation end portion which is placed facing the irradiation window portion and reciprocating along the longitudinal direction of the irradiation window portion, a transmitting member which transmits a reciprocation in a major axis direction of said insertion portion to cause said energy irradiation end portion to make reciprocating motion, a cylinder which is held to be rotatable about an axis parallel to an axis in the longitudinal direction and has a shaped portion which is formed on an outer surface and reciprocates said transmitting member, and a driving unit including a motor which rotates said cylinder.

2. The apparatus according to claim 1, wherein the shaped portion of said cylinder reciprocates said transmitting member at substantially a constant velocity, and sets a ratio of a time for direction change to a time for one reciprocating motion to not more than 35%.

3. The apparatus according to claim 1, wherein a ratio of an interval of motion with a constant velocity to a stroke of reciprocating motion is more than 70%.

4. The apparatus according to claim 1, wherein said cylinder comprises a hat-like member which is directly coupled to an output shaft of said motor and can incorporate said motor.

5. The apparatus according to claim 1, wherein the shaped portion comprises an endless groove which is continuously formed on the outer surface of said cylinder, and causes said transmitting member to make the reciprocation by causing said transmitting member to follow said endless groove.

6. The apparatus according to claim 5, wherein said endless groove causes said transmitting member to make one reciprocation or two reciprocations per rotation of said cylinder.

7. The apparatus according to claim 1, wherein
said energy irradiation end portion comprises a mirror placed facing a light exit of an optical fiber for energy transmission, and
a guide comprising an angle changing mechanism which changes a light exit angle of said mirror with respect to the irradiation window portion upon the reciprocal movement to make the mirror reflect energy output from the light exit of the optical fiber and direct the energy to a deep portion of living tissue.

8. The apparatus according to claim 7, wherein said transmitting member is the optical fiber.

9. The apparatus according to claim 7, wherein
said insertion portion incorporating said energy irradiation mechanism and said guide and said driving unit are configured to be separated from each other, and
said insertion portion is configured to be detachable from said driving unit by engaging a locked member fixed to the transmitting member with the endless groove of said cylinder.

10. The apparatus according to claim 1, wherein the energy comprises a laser beam.

11. The apparatus according to claim 1, wherein said energy irradiation end portion comprises an ultrasonic radiator.

12. An energy irradiation apparatus comprising:
an insertion portion which includes a hollow cylindrical member having a sealed distal end portion and is configured to be inserted into a living body, and an energy irradiation mechanism which is placed inside the hollow cylindrical member and radiates energy to living tissue through an irradiation window portion which is provided on a side wall of the hollow cylindrical member to extend in a longitudinal direction,
wherein said energy irradiation mechanism comprises an energy irradiation end portion which is placed facing the irradiation window portion and reciprocating along the longitudinal direction of the irradiation window portion, and driving a unit which drive said energy irradiation end portion to make reciprocating motion with substantially a constant velocity, and sets a ratio of a time for direction change to a time for one reciprocating motion to not more than 35%.

13. The apparatus according to claim 12, wherein a ratio of an interval of motion with a constant velocity to a stroke of reciprocating motion is more than 70%.

* * * * *